US009797006B2

(12) United States Patent
Niemz et al.

(10) Patent No.: US 9,797,006 B2
(45) Date of Patent: Oct. 24, 2017

(54) SYSTEM AND CARTRIDGE FOR EFFICIENT NUCLEIC ACID TESTING

(71) Applicant: Keck Graduate Institute of Applied Life Sciences, Claremont, CA (US)

(72) Inventors: Angelika Niemz, Claremont, CA (US); Anna Hickerson, Altadena, CA (US); Kristina Roskos, Los Gatos, CA (US); Hsiang-Wei Lu, Diamond Bar, CA (US)

(73) Assignee: Keck Graduate Institute of Applied Life Sciences, Claremont, CA (US)

( * ) Notice: Subject to any disclaimer, the term of this patent is extended or adjusted under 35 U.S.C. 154(b) by 227 days.

(21) Appl. No.: 13/860,453

(22) Filed: Apr. 10, 2013

(65) Prior Publication Data
US 2013/0267016 A1    Oct. 10, 2013

Related U.S. Application Data

(60) Provisional application No. 61/622,005, filed on Apr. 10, 2012, provisional application No. 61/799,776, filed on Mar. 15, 2013.

(51) Int. Cl.
*B01L 3/00*     (2006.01)
*B01L 7/00*     (2006.01)
*C12Q 1/68*     (2006.01)
*F04B 17/00*    (2006.01)

(52) U.S. Cl.
CPC .......... *C12Q 1/686* (2013.01); *B01L 3/50273* (2013.01); *F04B 17/00* (2013.01); *B01L 3/502723* (2013.01); *B01L 7/00* (2013.01); *B01L 2300/0663* (2013.01); *B01L 2400/046* (2013.01); *B01L 2400/0421* (2013.01); *B01L 2400/0481* (2013.01)

(58) Field of Classification Search
CPC ..... B01L 2300/0663; B01L 2400/0421; B01L 2400/046; B01L 2400/0481; B01L 3/502723; B01L 3/50273; B01L 7/00; C12C 1/686; F04B 17/00
USPC ..................... 435/6, 6.1, 287.1, 287.2, 288.7
See application file for complete search history.

(56) References Cited

U.S. PATENT DOCUMENTS

| 2002/0039783 | A1* | 4/2002 | McMillan et al. ......... 435/287.2 |
| 2002/0045851 | A1* | 4/2002 | Suzuki .................... A61M 1/28  604/28 |
| 2004/0037739 | A1* | 2/2004 | McNeely et al. ............... 422/58 |
| 2007/0154922 | A1* | 7/2007 | Collier et al. .................... 435/6 |

(Continued)

OTHER PUBLICATIONS

International Search Report and Written Opinion for corresponding International Patent Application No. PCT/US2013/036019, mailed Jul. 22, 2013, 12pp.

(Continued)

*Primary Examiner* — Kevin Joyner
*Assistant Examiner* — Holly Mull
(74) *Attorney, Agent, or Firm* — Lewis Roca Rothgerber Christie LLP

(57) ABSTRACT

A disposable and inexpensive biological diagnostic cartridge for the amplification and detection of nucleic acids includes a configuration having a reaction pouch for amplification which is compressed by a flexible pump pouch for detection of the amplified reaction.

17 Claims, 21 Drawing Sheets
(8 of 21 Drawing Sheet(s) Filed in Color)

(56) References Cited

U.S. PATENT DOCUMENTS

| | | | |
|---|---|---|---|
| 2008/0069732 A1* | 3/2008 | Yi | F04B 43/00 422/82.01 |
| 2009/0185955 A1 | 7/2009 | Nellissen | |
| 2009/0325276 A1 | 12/2009 | Battrell et al. | |
| 2010/0051124 A1* | 3/2010 | Imran | B01J 19/0093 137/565.11 |
| 2010/0056383 A1* | 3/2010 | Ririe et al. | 506/7 |
| 2012/0177543 A1* | 7/2012 | Battrell | B01F 11/0071 422/187 |

OTHER PUBLICATIONS

Do, Jaephil et al.; "Development of functional lab-on-a-chip on polymer for point-of-care testing of metabolic parameters"; Lab on a Chip; 2008; vol. 8; pp. 2113-2120.

Haeberle, Stefan et al.; "Microfluidic platforms for lab-on-a-chip applications"; Lab on a Chip; 2007; vol. 7; pp. 1094-1110.

Legally, E.T. et al.; "Single-Molecule DNA Amplification and Analysis in an Integrated Microfluidic Device"; Analytical Chemistry; vol. 73; No. 3; Feb. 1, 2001; pp. 565-570.

* cited by examiner

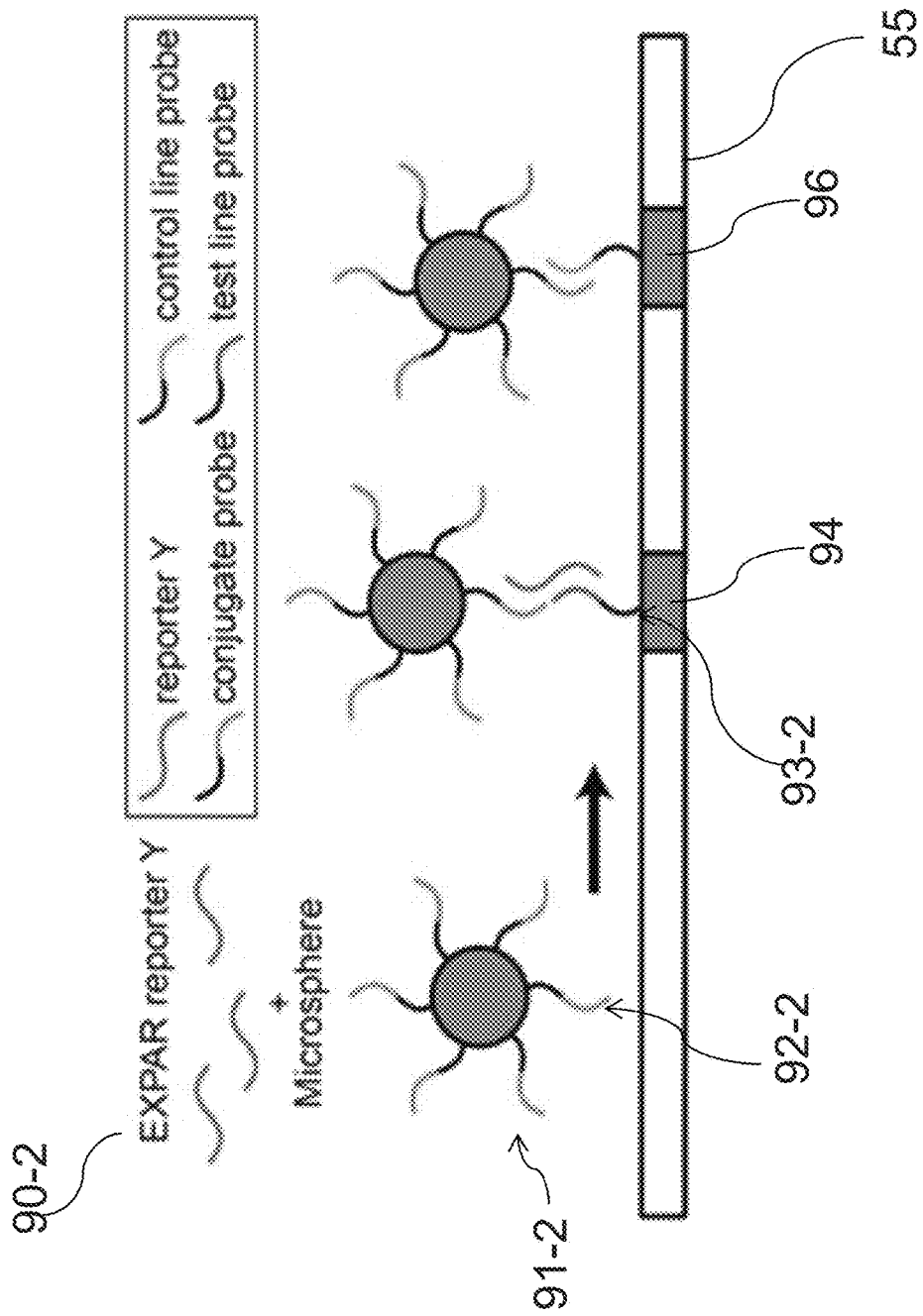

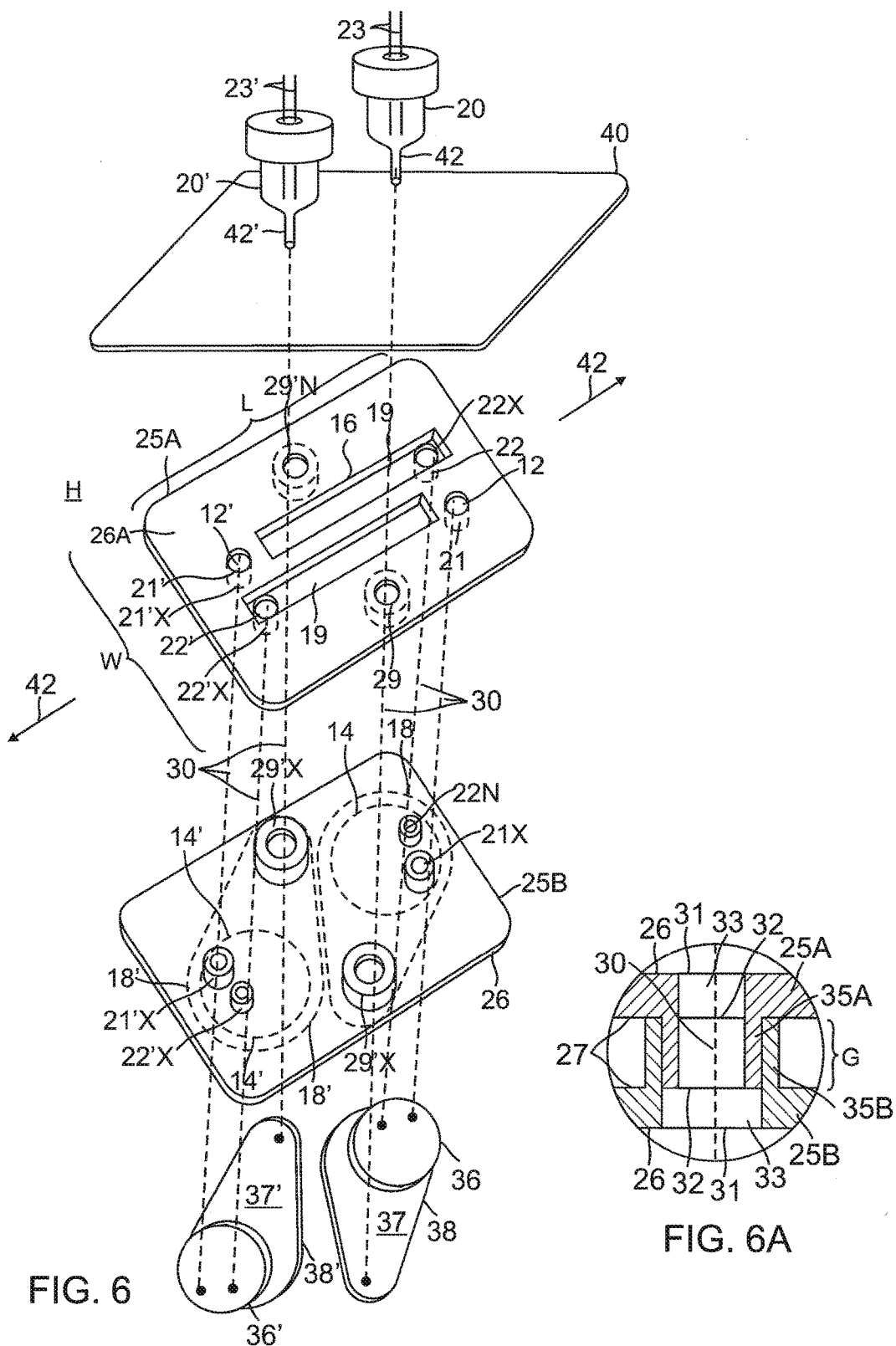

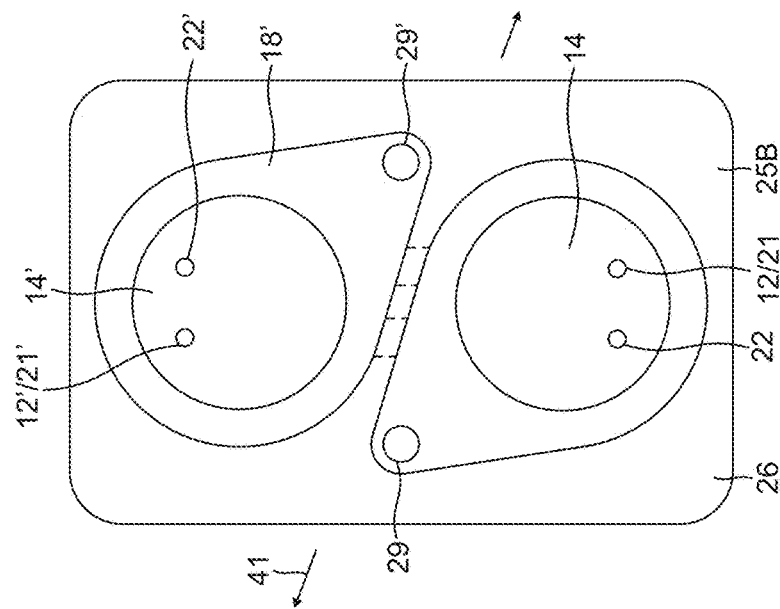
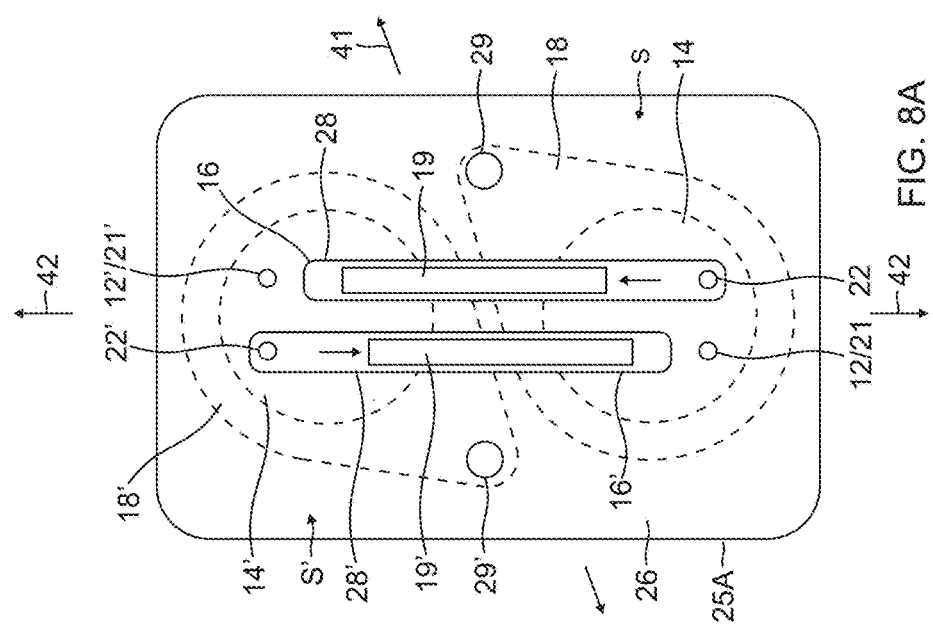

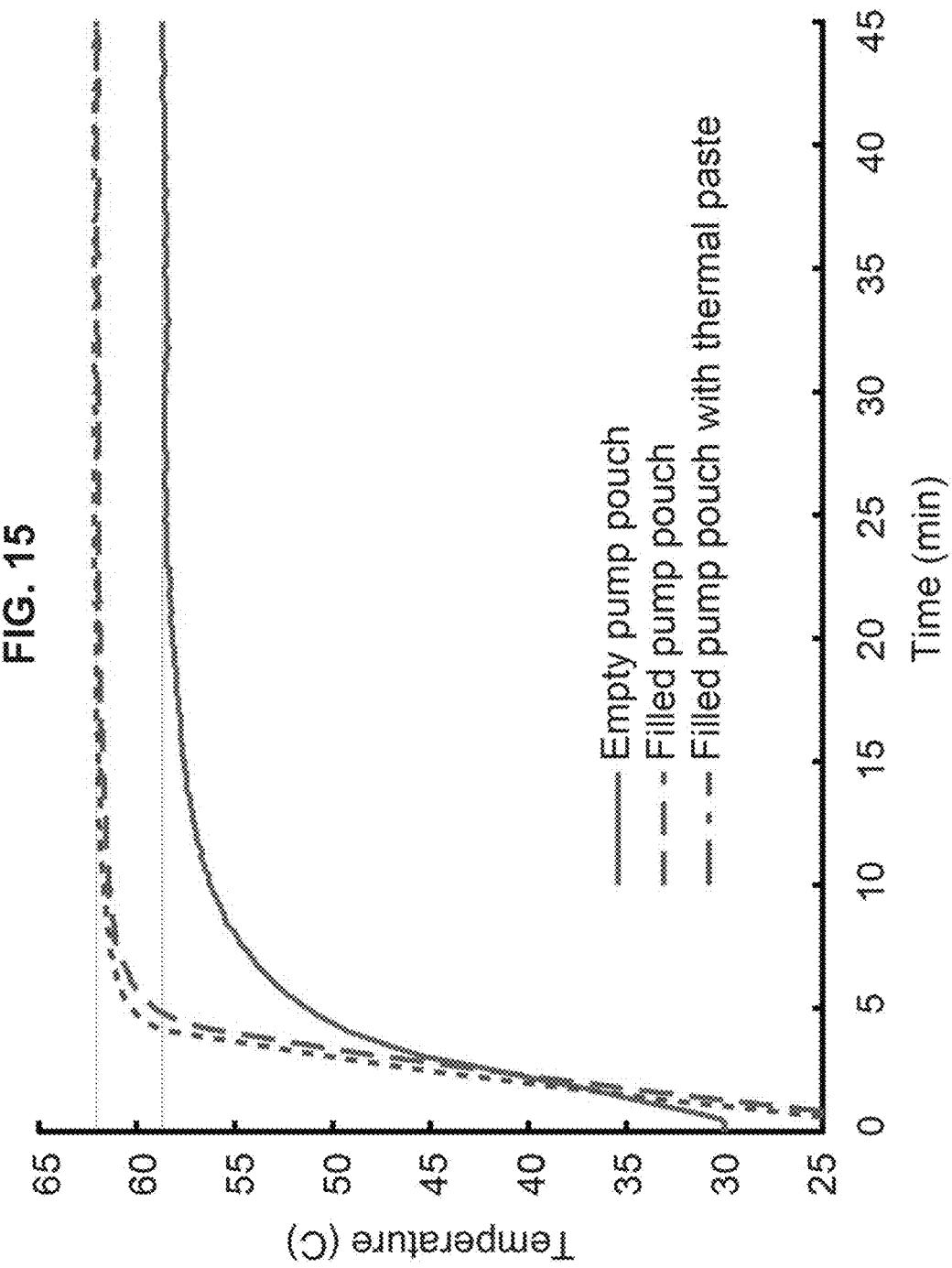

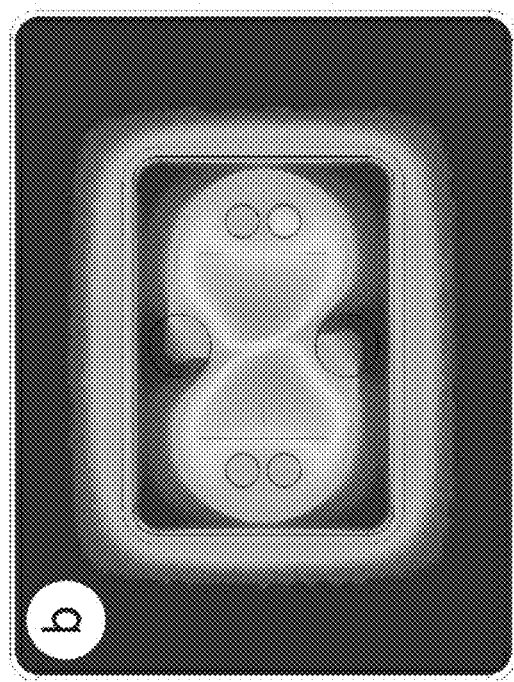
FIG. 16B
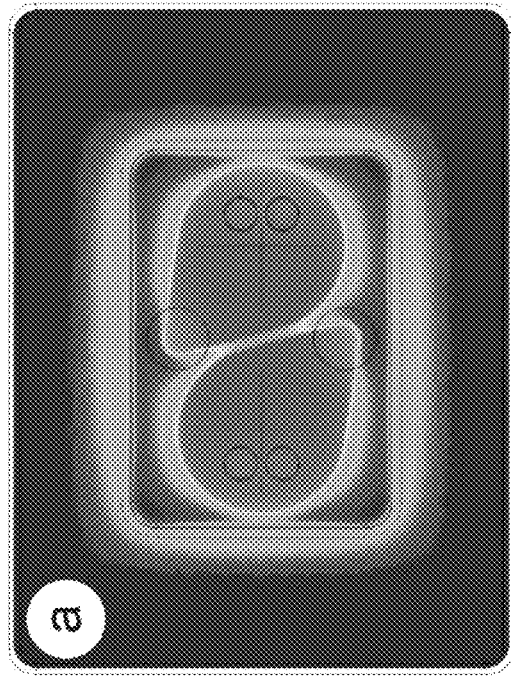
FIG. 16A
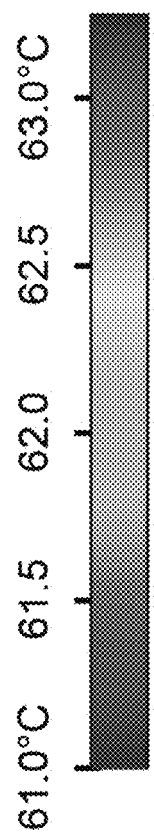

1kb ladder

SYSTEM AND CARTRIDGE FOR EFFICIENT NUCLEIC ACID TESTING

CROSS-REFERENCE TO RELATED APPLICATION(S)

The present application claims priority to and the benefit of U.S. Provisional Application Ser. No. 61/622,005 filed on Apr. 10, 2012, and U.S. Provisional Application Ser. No. 61/799,776 filed on Mar. 15, 2013, the entire contents of both of which are incorporated herein by reference.

STATEMENT REGARDING FEDERALLY SPONSORED RESEARCH OR DEVELOPMENT

This invention was made with government support under R01AI076247 and R01AI090831 awarded by the National Institutes of Health. The government has certain rights in the invention.

FIELD

This invention is directed to a cartridge for facile amplification and detection of nucleic acids for biological diagnosis.

BACKGROUND

Nucleic acid testing (NAT) can be used to diagnose infectious diseases by identifying the pathogen's genetic material. NAT is usually performed in centralized laboratories by highly trained personnel on large, complex, expensive equipment. However, testing in a central laboratory is not ideal for applications that require a rapid answer to facilitate treatment and improve patient outcomes. Additionally, in developing countries, the diagnosis of endemic infectious diseases through NAT in central laboratories is hampered by the lack of suitable facilities, trained personnel, and logistics chains.

Nucleic acid amplification testing (NAAT) enables sensitive and specific diagnosis of infectious diseases, producing accurate results in less than one day. However, most NAAT technologies require additional time for samples to be transferred to a central laboratory with results transferred back to the care provider. Point of care (POC) NAAT eliminates these often substantial additional delays and enables testing and treatment initiation in the same visit, which is more time efficient and may reduce the risk of losing a patient to delayed follow-up.

PCR-based fully or partially integrated NAAT systems for infectious disease diagnosis are in development or on the market, but all of these PCR-based systems are relatively expensive bench-top systems due to the complexity associated with thermocycling and real time fluorescence detection.

NAAT for infectious diseases requires sample input volumes to reach the required limit of detection (LOD)—which, in general, range from 100 μL to several mL. After sample preparation, the purified and concentrated DNA is combined with additional reagents, resulting in a master-mix volume between 30-100 μL which is then processed for amplification and detection. Mesofluidic systems are capable of processing samples in this volume range, including up to several hundred microliters. Since the attainable LOD scales linearly with sample input volume, this volume restriction places microfluidic systems (e.g., PCR systems) at a significant disadvantage. Moreover, real time PCR requires thermocycling and fluorescence optics for detection, and the fluorescence optics are difficult to implement in a compact, low cost, and robust instrument for use in low-resource settings. In contrast to PCR, isothermal NAAT requires a single reaction temperature, and therefore utilizes more simplified instrumentation than a PCR system.

Lateral flow devices work well for POC diagnostics because lateral flow devices can be manufactured inexpensively in large quantities, rely on passive fluidics, and provide a clear visual readout without additional instruments. While progress has been made in automating isothermal nucleic acid amplification, to date, users must perform sample preparation and amplification in separate manual steps, and then transfer the tube with the amplified master-mix for lateral flow detection. As such, there are currently no handheld inexpensive systems that automate and integrate isothermal nucleic acid amplification and lateral flow detection. Accordingly, a need exists for a low-cost, disposable cartridge in conjunction with a compact, inexpensive device that contains low power electronics, and is capable of processing a sample for nucleic acid amplification with lateral flow detection.

SUMMARY

The present invention is directed to a biological diagnostic cartridge assembly which has a housing that defines an inlet, a flexible reaction pouch downstream of the inlet, a flexible pump pouch adapted to compress the flexible reaction pouch, and a detection chamber downstream of the flexible reaction pouch. A biological sample introduced into the inlet travels downstream to the reaction pouch where reactions occur, including amplification in the presence of heat provided by a heat source. After amplification, amplified contents of the reaction pouch are transported to the detection chamber by means of a pump that expands the flexible pump pouch for compressing the flexible reaction pouch. In the detection chamber, the amplified contents are analyzed by a test strip. Accordingly, a fluid path is defined in the cartridge assembly to include a first path from the inlet to the flexible reaction pouch, and a second path from the flexible reaction pouch to the detection chamber.

In one embodiment, the pump comprises an electrolytic pump that is inserted into or otherwise joined with the cartridge assembly for fluid communication with the flexible pump pouch, which may contain a fluid that facilitates hydraulic pumping and enhances heat transfer. The flexible pump pouch is advantageously positioned in contact with and overlays at least a portion of the flexible reaction pouch, so as to exert a force on the flexible reaction pouch when the electrolytic pump is activated. The electrolytic pump is adapted to pump fluid at a flow rate that is generally a linear function of an applied current to its electrodes, which when energized cause production of gases that expand the flexible pump pouch against the flexible reaction pouch. In another embodiment, the electrolytic pump is integrated in the cartridge assembly with insert molded electrodes affixed in the housing of the cartridge assembly.

In one embodiment, the cartridge assembly includes a vent positioned upstream of the flexible reaction pouch and downstream of the inlet. The vent is adapted to permit gases to exit from the fluid path to outside the cartridge assembly. The vent may include a hydrophobic barrier that permits gases to exit the fluid path but retains liquid contents of the sample.

In one embodiment, the cartridge assembly includes a first one-way valve positioned upstream of the detection chamber and a second one-way valve upstream of the flexible reaction pouch.

In one embodiment, the test strip comprises a lateral flow test strip. The cartridge assembly provides an overflow pool region at a proximal end of the detection chamber to minimize the risk of flooding the flow strip in the detection chamber with contents entering the detection chamber from the flexible reaction pouch. The cartridge assembly also provides a waste chamber at a distal end of the detection chamber to collect waste fluid (e.g., gas) through a hydrophobic barrier.

In one embodiment, the housing has a two-piece construction with a top member and a bottom member, for example, of injection molded polycarbonate. Each member has alignment structures for joining the top and bottom members. In some embodiments, the alignment structures releasably join the top and bottom members. The top member has raised and recessed portions which form fluid paths and compartments when the members are joined together. An insert with flexible pouches may be provided for fluid connection with one of the members. One or both housing members may include openings to accommodate the insert and other structures of the housing and/or to provide visual access to the interior of the cartridge assembly. The housing may also include a thermal insulation material and/or a shock absorber cushion member positioned between the two housing members.

In a more detailed embodiment, the flexible reaction pouch and/or the flexible pump pouch comprises inserts formed from heat sealed thermoplastic film, for example, polypropylene. The inserts may be placed between the top and lower members of the housing for assembly therewith. Each insert may be a joined flexible reaction pouch and flexible pump pouch with the latter overlaying the former.

In a more detailed embodiment, the cartridge assembly comprises at least two amplification and detection systems, including a first inlet, a first flexible reaction pouch downstream of the first inlet, a first flexible pump pouch adapted to compress the first flexible reaction pouch, a first detection chamber downstream of the first flexible reaction pouch, a second inlet, a second flexible reaction pouch downstream of the second inlet, a second flexible pump pouch adapted to compress the second flexible reaction pouch, and a second detection chamber downstream of the second flexible reaction pouch. Each detection chamber includes a respective test strip.

In another embodiment, the cartridge assembly comprises at least one amplification and detection system, including an inlet, a fluid conduit, a reagent chamber with reagents, a vented fluid conduit with a hydrophobic barrier, a fluid conduit with a one-way passive inlet valve, a reaction chamber, a fluid conduit with a one-way outlet valve, a detection chamber and a waste chamber.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3B is a schematic illustration of exponential amplification reaction (EXPAR) detection of the "Y" oligonucleotide amplicons.

FIG. 6 is an exploded perspective view of the cartridge assembly of FIG. 4.

FIG. 6A is a detailed side cross-sectional view of an alignment through-hole of the cartridge assembly of FIG. 6.

FIG. 8A is a top plan view of a first housing member of the cartridge assembly of FIG. 4.

FIG. 8B is a bottom plan view of a second housing member of the cartridge assembly of FIG. 4.

FIG. 15 is a graph of temperature as a function of time for an empty pump pouch, a filled pump pouch and a filled pump pouch with thermal paste.

FIGS. 16A and 16B are thermal simulations of a cartridge on a heater, showing horizontal cross-sections within the center of the reaction pouch of the cartridge, according to embodiments of the present invention.

DETAILED DESCRIPTION

The present invention is directed to a system, and related methods and devices, for low-cost, disposable, pouch-based, isothermal nucleic acid amplification and detection (NAAD). The system utilizes a pumping method such as electrolytic pumping to move fluids within a pouch-based cartridge assembly. The present system is adapted to apply isothermal nucleic acid amplification methods. Isothermal nucleic acid amplification methods are known in the art, and any suitable means for this isothermal amplification may be used with the presently disclosed system. An example of isothermal nucleic acid amplification includes the loop-mediated isothermal amplification (LAMP). LAMP uses four to six oligonucleotide primers that recognize multiple sequences in a target DNA and the LAMP reaction generates concatenated DNA products with high molecular weight and extensive secondary structure. Methods for LAMP are known and are described, for example, in Iwamoto et al., 2003, *J. Clin. Microbiol.* 41, 2616-2622, the entire contents of which are herein incorporated by reference. Accordingly, some embodiments of the present system for amplifying DNA of a sample is configured to process the sample using LAMP.

As another example, the present system may be adapted to use Exponential Amplification Reaction (EXPAR), which amplifies short trigger oligonucleotides at a constant 55° C. using polymerase and nicking enzyme activities, as described in Van Ness et al., 2003, *PNAS,* 100, 4504-4509, the entire contents of which are herein incorporated by reference. Accordingly, some embodiments of the cartridge system for amplifying the DNA of the sample are configured to process the sample using EXPAR. Any isothermal nucleic acid amplification may be used with the disclosed cartridge and system as any adaptation can be readily determined from this disclosure and known techniques.

Figure 3A:
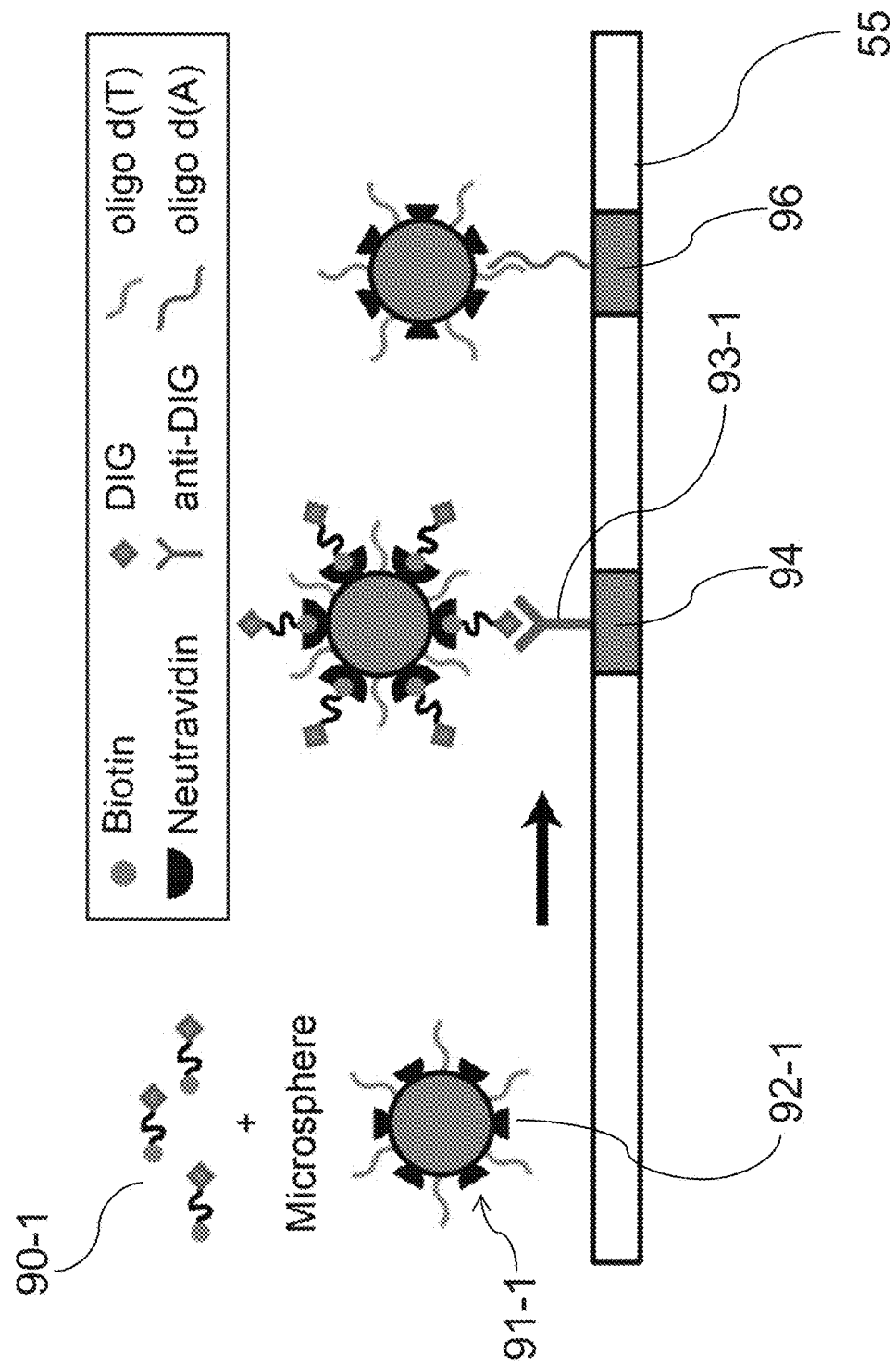
FIG. 3A is a schematic illustration of antibody-dependent nucleic acid lateral flow (NALF) detection of amplicons produced from loop-mediated isothermal amplification (LAMP).

The present system is further adapted to incorporate a means for detection of the amplified reaction. Non-limiting examples of detection methods include nucleic acid lateral flow (NALF), paper-based microfluidics, and dried reagent slide analysis. NALF detection may include either antibody-dependent or antibody-independent configurations for end-point detection of the reaction, with the sensitivity contingent upon upstream amplification. As shown in FIG. 3A. antibody-dependent NALF has been used to detect LAMP products by incorporating antigenic labels or haptens into the amplicon to form a labeled amplicon 90. Examples of haptens include biotin and dioxigenin (DIG) which bind with high affinity to avidin and anti-dioxigenin antibodies, respectively. NALF detection of the labeled amplicon 90-1 is then performed using a microsphere (91-1) conjugated with the cognate binding partner (e.g., neutravidin) 92-1 and/or an antibody (e.g., anti-DIG) 93-1 that is specific to the label(s) conjugated to the test strip 55 at test region 94 with a control region 96, as shown in FIG. 3A. For antibody-independent NALF, unlabeled target amplicons are directly hybridized to colored oligonucleotide-functionalized microparticles and immobilized oligonucleotides on the test strip membrane.

For detection analysis of EXPAR amplification, as shown in FIG. 3B, the EXPAR reporter "Y" oligonucleotide amplicons 90-2 bind with the 5' and 3' consensus sequence probes 92-2, 93-2 of the Y reporter. One Y probe 92-2 is conjugated to a microsphere 91-2 and the other Y probe 93-2 is conjugated to the test region 94 of the test strip 55.

In order to integrate isothermal DNA amplification (e.g., LAMP or EXPAR amplicons) with NALF detection in a single device, the system of the present invention provides an amplified mixture by heating a master-mix at a fixed temperature for a set time, and then pumping the amplified mixture onto a lateral flow strip, for example, by providing a fluid pump actuated by an electrolysis pump. Electrolysis is an inexpensive method to pump fluids. For example, hydrogen and oxygen gas generated by a water electrolytic pump can be used to exert pressure on a fluid for displacement at a flow rate proportional to the applied current. Because of these advantageous features, some embodiments of the NAAD system of the present invention are used for diagnosing infectious disease, for example, *Mycobacterium tuberculosis* (M.tb), however the invention is not limited thereto.

Figure 1:
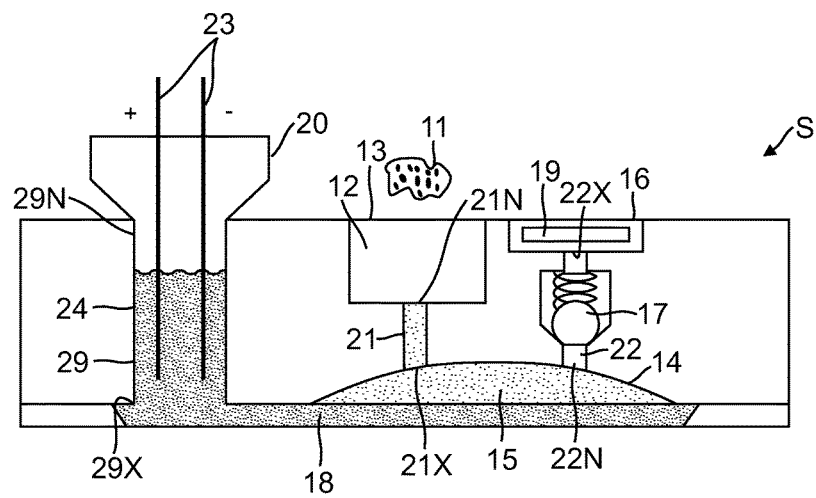
FIG. 1 is a schematic illustration of an amplification and detection system in accordance with one embodiment of the present invention, with a master mix in a reaction chamber.
Figure 2:
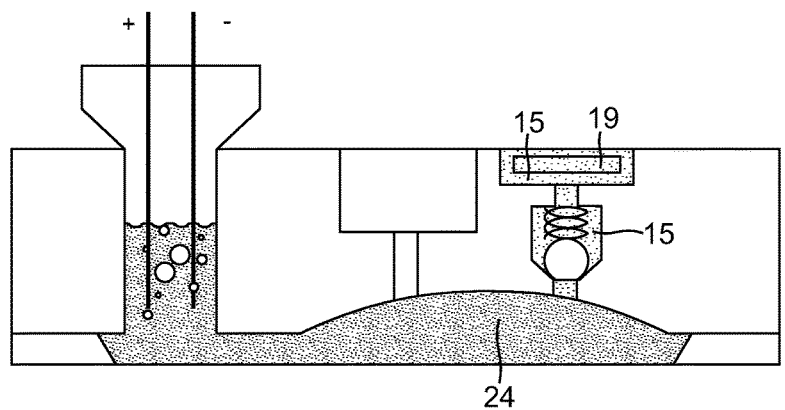
FIG. 2 is a schematic illustration of the system of FIG. 1, with the master mix transported to a detection chamber.

With reference to FIGS. 1 and 2, the system S of the present invention includes a fluid path connecting and providing fluid communication between at least an inlet 13 (with or without a septum 12) for receiving a biological sample 11, a reaction chamber 14 for amplification of a master mix 15 comprising reagent(s) and the sample, and a detection chamber 16 containing a test strip 19. The system S also includes a fluid pump 18 that is in direct pressure contact with the reaction chamber 14, and an electrolytic cell 20 which comprises electrodes 23 and electrolyte 24 to actuate the fluid pump 18 for compressing the reaction chamber 14 to deliver the master mix 15 to the detection chamber 16 (FIG. 2). One or more one-way valves 17 are provided in the system S to control and regulate fluid flow. With multiple fluid conduits, including a first fluid conduit 21 (with entry 21N and exit 21X) between the inlet 13 and the reaction chamber 14 and a second fluid conduit 22 (with entry 22N and exit 22X) between the reaction chamber 14 and the detection chamber 14, the system S defines a fluid path from upstream to downstream of at least the inlet 13 through the first fluid conduit 21 to the reaction chamber 14 and through the second fluid conduit 22 to the detection chamber 16. The system S may also include a third fluid conduit 29 (with entry 29N and exit 29X) between the electrolytic cell 20 and the fluid pump 18 to facilitate activation of the fluid pump.

In use, the system S receives the sample 11 in the inlet 13, e.g., via the septum 13. In this S system, the injected sample is a complete master mix 15 including sample nucleic acids and amplification reagents. This master mix sample (11, 15) enters the reaction chamber 14, e.g., by injection with a syringe, via the first fluid conduit 21 for amplification where it is heated. After the master mix in the reaction chamber 14 has been exposed to a predetermined temperature for a predetermined duration of time for amplification, the electrolytic pump 20 is activated by provision of electrical current to the electrodes 23 which generates gas causing the fluid pump 18 to expand and press against the reaction chamber, thereby transporting the master mix 15 of the reaction chamber 14 to the detection chamber 16, as shown in FIG. 2. The one-way valve 17, for, example, a one-way passive inlet check valve, is situated in the second fluid conduit 22 between the entry 22N and the exit 22X to control and regulate fluid flow between the reaction chamber 14 and the detection chamber 16, including limiting fluid flow of the contents of the reaction chamber 14 to a downstream direction from the reaction chamber 14 to the detection chamber 16.

Cartridge Assembly Configuration

The system S of the present invention is conveniently embodied in a cartridge assembly that is disposable and small in size, and inexpensive to manufacture. Components of the cartridge assembly are advantageously made using inexpensive and scalable methods. Moreover, the cartridge assembly is portable and may be held in the hand of the user, with dimensions which are no more than about 10 inches in any direction, and more preferably ranging between about 2.5 inches to 5.0 inches in any direction.

Figure 4:
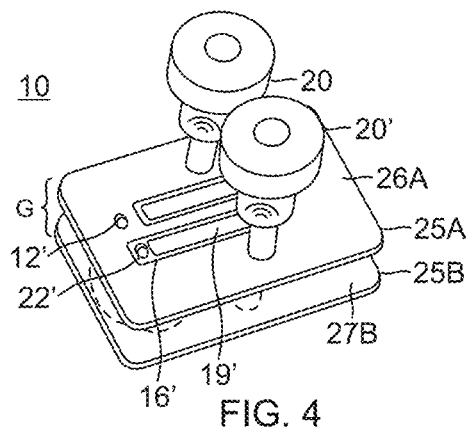
FIG. 4 is a perspective view of a cartridge assembly in accordance with one embodiment of the present invention.

In the illustrated embodiment of FIG. 4, the cartridge assembly 10 includes a fabricated support structure H1 that houses, supports and defines a first system S and a second system S'. However, as would be apparent to one of ordinary skill in the art, the cartridge assembly 10 may house a single system or more than two systems, as desired or appropriate. In the illustrated embodiment, counter-part components of the systems S and S' are identified by similar reference numerals, with the components of the system S' being distinguished by a "prime" designation.

Figure 5:
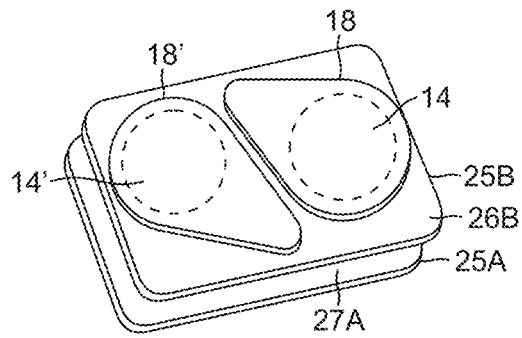
FIG. 5 is a bottom perspective view of the cartridge assembly of FIG. 4.
Figure 7:
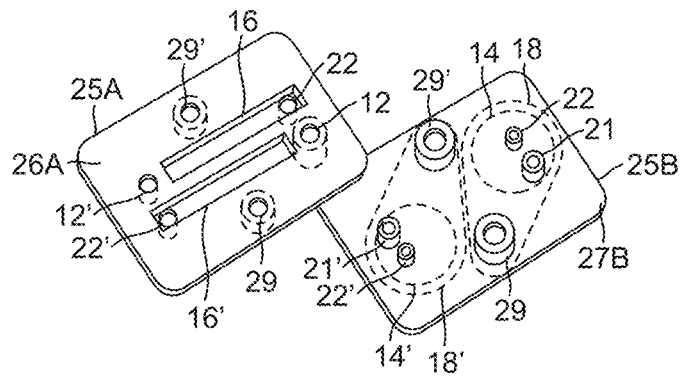
FIG. 7 is a perspective view of an unassembled housing structure of the cartridge assembly of FIG. 4.

With further reference to FIGS. 5, 6 and 7, the housing structure H1 comprises a first or top planar member (or card) 25A, and a second or bottom planar member (or card) 25B. The cards are of a generally rigid construction, with a similar size and shape. As illustrated, each card has a generally rectangular shape, although it is understood that other shapes are suitable, for example, square, circular, polygonal or irregular. Each card has a greater length dimension L, a lesser width dimension W and a thickness dimension T. The cards may be constructed of any suitable material, for example, a polymer and polycarbonate. The cards 25A and 25B are arranged in a stacked configuration, one overlying the other, in general vertical alignment with each other. So arranged, each card may be defined as having a generally flat outer surface 26 and a generally flat inner surface 27, wherein the inner surface 27 of each card faces inwardly toward each other and the outer surface 26 of each card faces outwardly away from each other.

Extending through the thickness dimension T of each of the first card 25A and the second card 25B are a plurality of correspondingly aligned through-holes, each represented by a broken line 30 in FIG. 6. A detailed view of an aligned pair of through-holes 30 between cards 25A and 25B is shown in FIG. 6A. Each through-hole 30 has an opening 31 on the outer surface 26, an opening 32 on the inner surface 27, and a channel 33 therebetween which allows fluid communication through the thickness of the card between its outer surface 26 and inner surface 27. In the illustrated embodiment, the inner surface 27 of each card 25A and 25B has a raised cylinder or ring 35A and 35B, respectively, which matingly engages each other as a male connector and a female connector. In this manner, the channels 33 of an aligned pair of through-holes 30 of the cards 25A and 25B are joined and connected to form a generally sealed, fluid-tight conduit between the cards 25A and 25B. The raised rings 35A and 35B provide a gap G between the cards 25A and 25B, all or portion(s) of which may be filled with thermal insulation and shock absorbing material, such as polyurethane foam or silicone foam. As such, selected through-holes serve as the inlet 13, the first conduit 21 and the second conduit 22 between the cards 25A and 25B of the system S. For purposes of facilitating the description of the systems S and S', the description herein is directed to the components of the system S, although it is understood that the description applies equally to the components of the system S'.

With further reference to FIGS. 1 and 6, to form the reaction chamber 14 and the fluid pump 18 of the system S, a plurality of layered flexible pouches are formed on the outer surface 26 of the bottom card 25B by a first layer of thin thermoplastic film patch 36 and a second layer of thin thermoplastic film patch 37. The larger outer film patch 37 extends over at least a portion, if not all, of the smaller inner film patch 36. Outer peripheral edges 38 of the film patch 36 and 37 are affixed and sealed, e.g., with adhesives, thermal bonding (heat sealed) and/or ultrasonic welding, to the outer surface 26 of the bottom card 25B. The smaller film patch 36 is positioned on the outer surface 26 of the bottom card 25B to extend over and cover the first fluid conduit exit 21X and second fluid conduit entry 22N. The larger overlying film patch 37 is positioned over at least a portion of the reaction pouch 14 and an exit 29X of a third fluid conduit 29 that provides fluid communication between the electrolytic cell 20 and the fluid pump pouch 18. In that regard, the third fluid conduit 29 is configured to receive at its entry 29N a nozzle 42 of the electrolytic cell 20 with electrolytic fluid 24 for activating the fluid pump pouch 18.

In the illustrated embodiment, the smaller inner film patch 36 has a circular shape and the larger outer film patch 37 has a generally triangular or tear-drop shape. Both shapes correspond with locations of selected components of the system S, including the fluid conduits 21, 22 and/or 29, as described above. Accordingly, it is understood that the film patches may have different shapes and sizes where the system S is configured differently in and on the cartridge assembly 10.

To provide the detection chamber 16, the outer surface 26 of the top card 25A is formed with a shallow recessed groove 28. The groove has a depth sufficient to contain test strip 19. To seal the detection chamber 16, a thin and generally transparent thermoplastic film sheet 40 is applied to at least the outer surface 26 of the top card 25A to extend over at least the groove 28 and the second fluid conduit exit 22X. The nozzle 42 of the electrolytic cell 20 is inserted into the entry 29N of the third fluid conduit 29. Moreover, the film 40 is also punctured when the sample 11 is injected into the inlet 13 by a syringe. As mentioned, the foregoing description applies to the components of S' which are identified by similar reference numbers with a prime designation, as shown in the Figures.

As better illustrated in FIGS. 8A and 8B, the systems S and S' are arranged on and in the card assembly 10 generally inversely opposite to each other across a diagonal axis with the grooves 28 and 28' defining the detection chambers 16 and 16' in an anti- or oppositely parallel configuration along a longitudinal axis 42. This arrangement and configuration provide for efficient use of the space available in and on the cards 25A and 25B, although it is understood that other arrangements and configurations (with one or two or more systems) are also suitable to provide for efficient use of cartridge assembly space.

The cartridge assembly 10 is assembled by snap-fitting the cards 25A and 25B together with the inner surfaces 27 facing each other and the through-holes 30 vertically aligned. Although FIG. 6A shows a male ring 35A formed on the inner surface 27 of the top card 25A and a female ring 35B formed on the inner surface 27 of the bottom card 25B, it is understood that any of the through-holes may be formed by a male ring formed on the inner surface of the bottom card 25B with the female ring formed on the inner surface of the top card 25A. The film patches 36, 36', 37 and 37' may be affixed to the outer surface 26 of the bottom card 25A to form the flexible reaction pouches 14, 14' and flexible pump pouches 18 and 18' before or after the cards 25A and 25B are joined. Moreover, the test strips 19 and 19' may be placed into the grooves 28 and 28' before or after the cards are joined and before or after the pouches are formed. After the test strips 19 and 19' are placed into the grooves 28 and 28', the thin film sheet 40 is affixed to the outer surface 26 of the top card 25A to seal the test strips in the detection chambers 16 and 16'.

So assembled, the disclosed embodiment of the cartridge assembly 10 provides a first and a second NAAD systems S and S'. For the system S, a fluid path leads from the inlet 13 on or near the top or outer surface 26 of the top card 25A to the first fluid conduit 21 which provides fluid flow from the inlet 13 to the reaction pouch 14 at the bottom or outer surface of the bottom card 25B. The second fluid conduit 22 provides fluid flow from the reaction pouch 14 to the detection chamber 16 on or near the top or outer surface 26 of the top card 25A where the test strip 19 is located and readily visible to a user of the card assembly 10. The one-way passive outlet check valve 17 is oriented to pass fluid from the reaction pouch 14 to the detection chamber 16 but not vice versa. The one-way flow may also be provided by an active valve or by any other suitable methods. The electrolytic cell 20 which activates the underlying pump pouch 18 to compress the overlying reaction pouch 14 is placed in fluid communication with the pump pouch 18 by inserting the nozzle 42 through the film 40 and into the third fluid conduit 29 from the top or outer surface 26 of the top card 25A. After the electrolytic solution 24 is injected into the cell 20 and the pump pouch 18, an electrical current is provided to the electrodes 23 which drive the cell 20 to expand the pump pouch 18. The cell 20 may be installed on the card assembly 10 after the thin film sheet 40 is placed on the top card 25A. The nozzle 42 is adapted to puncture the thin film sheet 40 as it is inserted and received in the third fluid conduit 29. The foregoing description also applies to the system S' as it functions identically to the system S.

Figure 9:
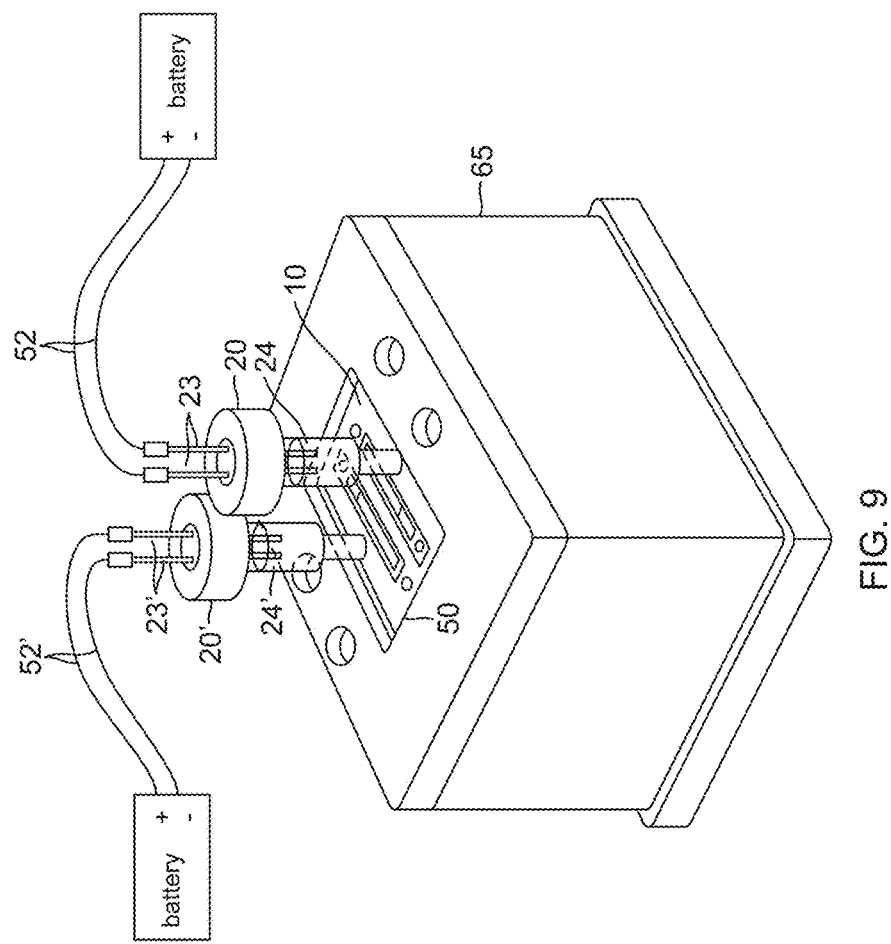
FIG. 9 is a perspective view of a cartridge assembly in use with a facilitator electronics unit of the present invention, in accordance with one embodiment.

The cartridge assembly 10 may be used in combination with a facilitator electronics unit 65, as shown in FIG. 9. For amplification, contents of reaction pouch 14 are heated by a heat source provided in the unit 65 which has a recessed receiving portion 50 in which the card assembly 10 is placed for thermal contact with a controlled heating surface generally lining the bottom of the recessed receiving portion 50. In that regard, it is understood that an empty card assembly 10 may be placed in the unit 65 and preheated to a reaction temperature. A reaction temperature may vary depending on the selected amplification method. In some embodiments, the reaction temperature is constant, and in the range of about 37° to 70° C. In some embodiments, the reaction temperature is constant at about 63° C. In other embodiments, the reaction temperature is constant at about 55° C.

In use, the cartridge assembly 10 may be placed in the unit 65 for preheating. After the cartridge assembly is heated to the selected reaction temperature, a reaction master-mix which contains both sample and amplification reagents is injected into the preheated reaction pouch 14 through the inlet 13, e.g., by a syringe, to thereby initiate isothermal DNA amplification. It is understood that the sample is introduced into the inlet 13 with sufficient pressure or injection force so as to travel into the reaction pouch 14. Once the amplification reaction is completed, a current is applied to the electrodes 23 by leads 52 connected to a current source 55, such as a battery, which may be integrated in or separate from the unit 65. With a current applied, the electrolytic cell 20 produces gas which expands the pump pouch 18 which in turn directly compresses the reaction pouch 14. When the reaction pouch 14 is compressed, the pressure in the pouch 14 increases until the valve 17 releases and allows the contents to exit and enter the second fluid conduit 22. The content passes into the detection chamber 16 and onto the test strip 19, e.g., a lateral flow test strip. The reaction mixture migrates along the test strip based on lateral flow (i.e., passive capillary action), producing a visual readout that is visible to the user from the detection chamber 16 through the thin film 40. In this process, fluids remain sealed within the cartridge assembly 10, eliminating amplicon carry-over contamination.

As shown in FIG. 9, the cartridge assembly 10 contains two NAAD systems allowing for two samples to be tested simultaneously, but the cartridge assembly 10 can contain any number of pouches, taking size and portability into consideration.

Figure 10:
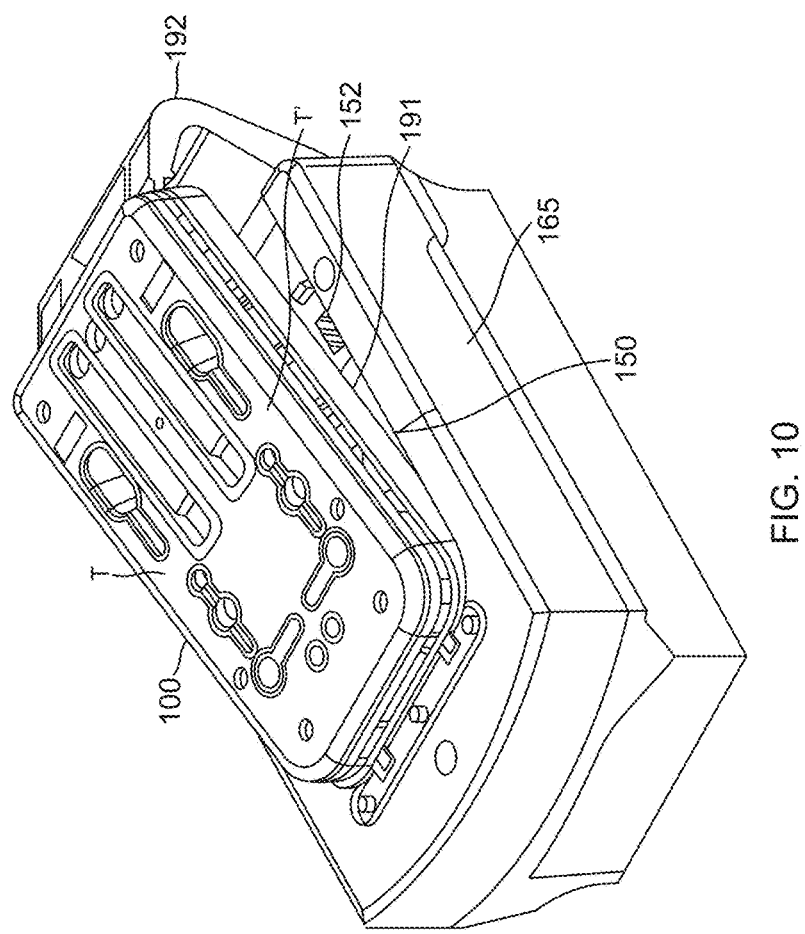
FIG. 10 is a perspective view of a cartridge assembly in use with a facilitator electronics unit of the present invention, in accordance with another embodiment.
Figure 11:
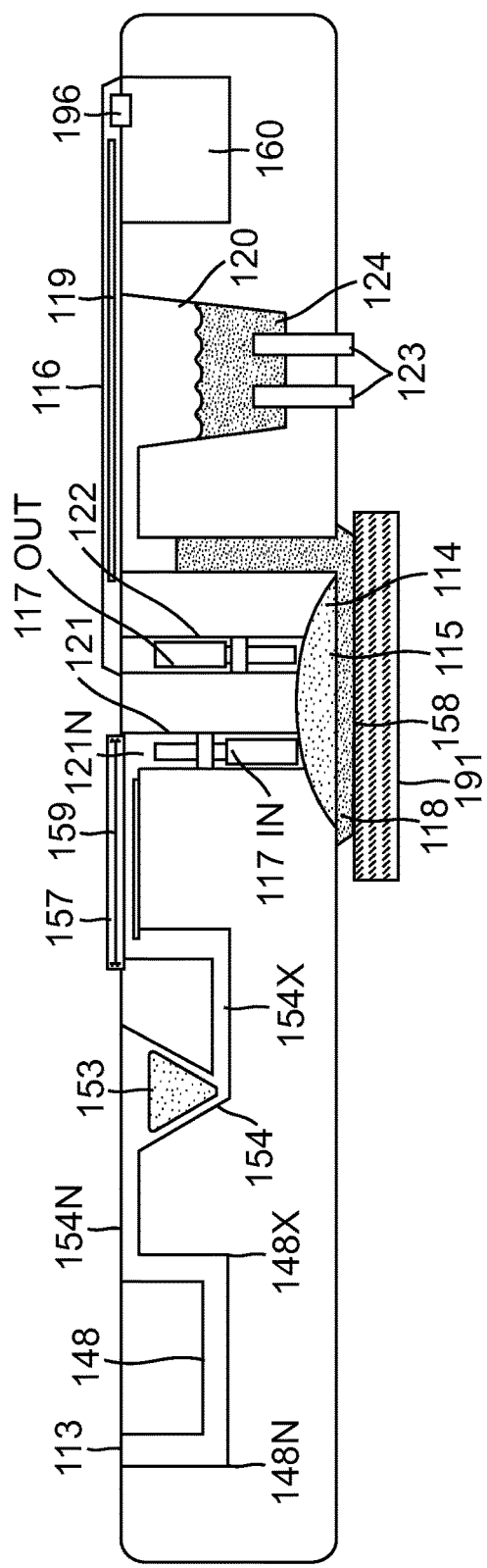
FIG. 11 is a schematic illustration of an amplification and detection system embodied in the cartridge assembly of FIG. 10.
Figure 12:
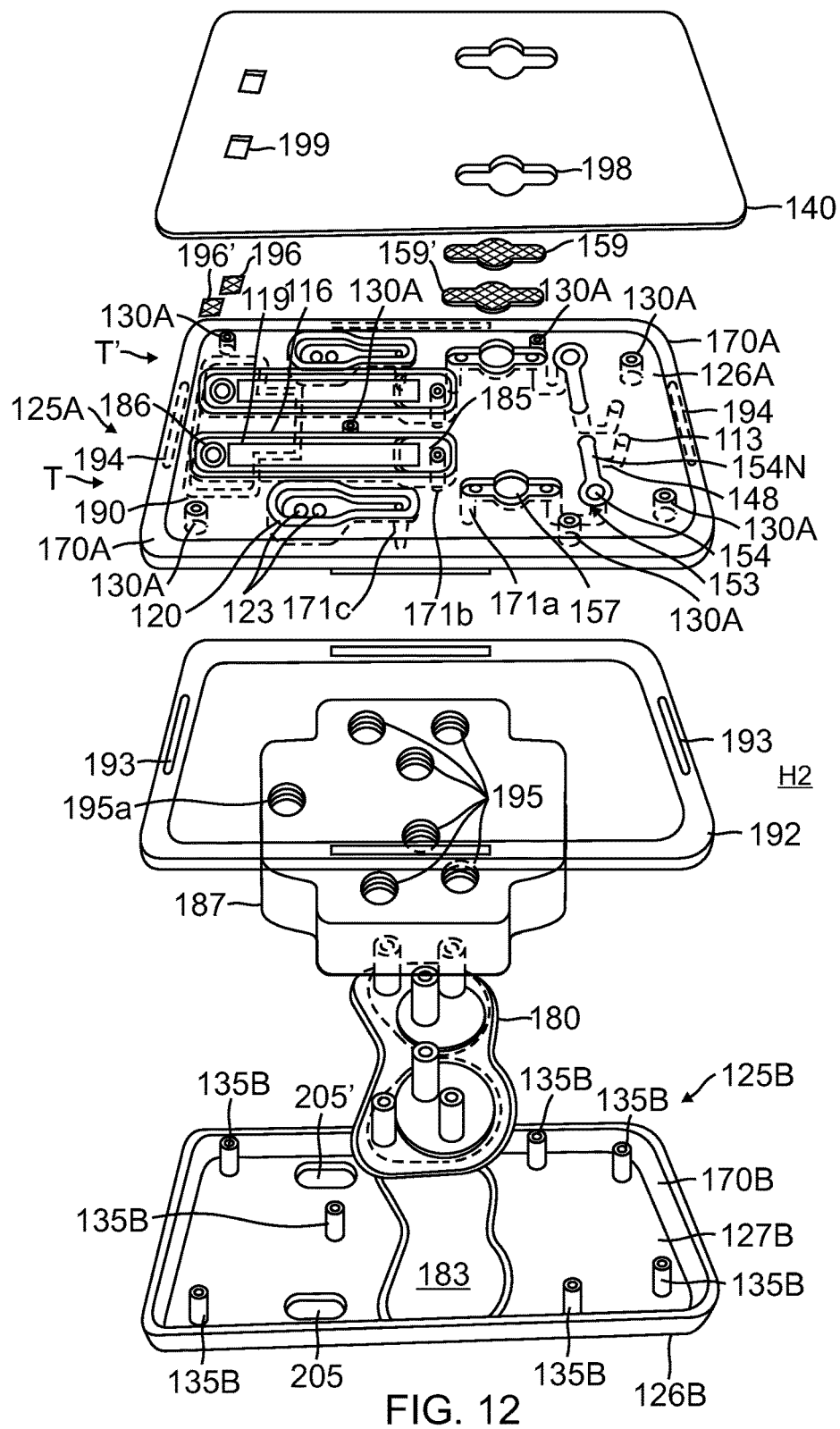
FIG. 12 is an exploded perspective view of the cartridge assembly of FIG. 10.

An alternate embodiment of the invention is illustrated in FIGS. 10-12. A cartridge assembly 100 is provided, with similarities to the aforementioned assembly 10 in terms of function, structure and components which are identified by similar reference numerals. Accordingly, the aforementioned description is applicable to the assembly 100, and vice versa. However, there are also differences between the two assemblies, including those illustrated and/or as discussed below. In the illustrated embodiment, the cartridge assembly 100 includes a fabricated support structure H2 that also houses, supports and defines a first system T and a second system T'. As would be apparent to one of ordinary skill in the art, a cartridge assembly 100 may house a single system or more than two systems, as desired or appropriate. In the illustrated embodiment, counter-part components of the systems T and T' are identified by similar reference numerals, with the components of the system T' being distinguished by a "prime" designation.

With reference to FIG. 11, the system T includes an inlet 113 (with or without a septum), a fluid conduit 121 (with entry 121N and exit 121X) leading to a reaction chamber or pouch 114, a fluid conduit 122 (with entry 122N and exit 122X) leading from the reaction pouch 114, and a detection chamber 116 with a test strip 119. A one-way passive inlet check valve 171N is press-fitted or otherwise positioned in the conduit 121 and a one-way passive outlet check valve 117OUT is press-fitted or otherwise positioned in the conduit 122. The system T also includes a fluid pump pouch 118 in direct pressure contact with the reaction pouch 114. The fluid pouch 118 contains pump fluid 170 and is activated by an electrolytic cell 120 having electrodes 123 and electrolyte 124. In the illustrated embodiment, the system T further includes a reagent chamber 154 followed by a vented fluid conduit 157 that are downstream of the inlet 113 and upstream of the reaction pouch 114, and a waste chamber 160 downstream of the detection chamber 116. In one embodiment, a fluid conduit 148 (with entry 148N and exit 148X) connects the inlet 113 and the reagent chamber 154. The reagent chamber 154 is optional and may improve the flow and mix of reagents, but is not required for providing the input sample into the reaction pouch if reagents are provided by another means. The reagent chamber 154 is not limited to a particular shape or configuration. As shown in FIG. 11, the shape of the reagent chamber is triangular, but the reagent chamber is not limited to the shape and can be any suitable shape. For example, the reagent chamber may be oval in shape to allow for pooling of the sample with reagent(s) 153. The reagent chamber 154 has an entry 154N and an exit 154X and may contain reagent(s) 153. The vented fluid conduit 157 has a hydrophobic barrier 159. The one-way inlet passive check valve 117IN is provided to regulate fluid flow into the reaction pouch 114. The one-way outlet passive check valve 117OUT regulates fluid flow out of the reaction pouch 114 and into the detection chamber 116. Accordingly, a fluid path of system T includes at least the inlet 113, the fluid conduit 148, the reagent chamber 154, the vented fluid conduit 157, the fluid conduit 121 with the inlet valve 117IN, the reaction pouch 114, the fluid conduit 122 with the outlet valve 117OUT, the detection chamber 116 and the waste chamber 160.

The system T is conveniently embodied in card assembly 100. In the illustrated embodiment of FIG. 12, the card assembly 100 has a housing structure H2 housing an insert 180 with flexible reaction pouch 114 and flexible pump pouch 118, and optionally an insulation member 187. The structure comprises a first or top member 125A providing, e.g., a core platform, and a second or bottom member 125B providing, e.g., a casing. The platform 125A and the bottom casing 125B each have a generally rectangular shape, although it is understood that other shapes are suitable. Each member 125A and 125B has a generally rigid planar body and may be defined as having an outer surface 126 and an inner surface 127, wherein the inner surface 127 of each member faces inwardly toward each other and the outer surface 126 of each member faces outwardly away from each other. Each member also has an outer peripheral flange 170A and 170B that extends perpendicularly so that when the members are joined the planar bodies and the flanges enclose an interior volume of space which is occupied at least partially by the insert 180 and the insulation member 187. To that end, the bottom member 125 has an opening 183 with a shape and size that correspond with but are slightly smaller than the shape and size of the insert 180 so that the insert 180 is secured between the members 125A and 125B while the flexible pouches 114 and 118 can freely expand without interference from the bottom member 125B. The members 125A and 125B may be made of any suitable material, including plastic, including polycarbonate.

Figure 12A:
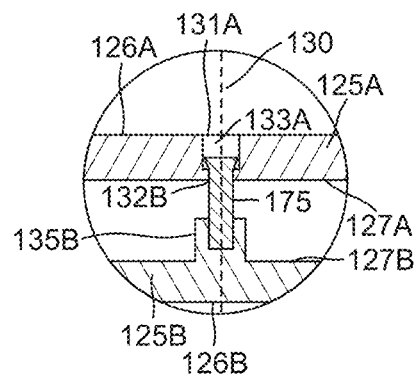
FIG. 12A is a detailed side cross-sectional view of an alignment and releasably fastening feature of the cartridge assembly of FIG. 10.

With reference to FIG. 12A, the inner surface 127 of one of the top or bottom members 125A and 125B has a plurality of alignment projections 135 for receiving screws 175 inserted through alignment channels 133 formed in the other of the top or bottom members. In the illustrated embodiment, the inner surface 127B of the bottom member 125B has the alignment projections 135B and the top member 125A has the corresponding alignment channels 133A extending between openings 131A and 132A, to form alignment bores 130 for the screws 175. In the illustrated embodiment, the top and bottom members 125A and 125B have seven corresponding alignment bores 130 for seven screws, e.g., four in the four corners of the housing, and two near the peripheral edge and one in an interior region.

In the embodiment of FIG. 12, the cartridge assembly 100 defines the systems T and T'. However, as would be apparent to one of ordinary skill in the art, the cartridge assembly 100 may house a single system or more than two systems, as desired or appropriate. In the illustrated embodiment, counter-part components of the systems T and T' are distinguished with a "prime" designation.

Figure 13:
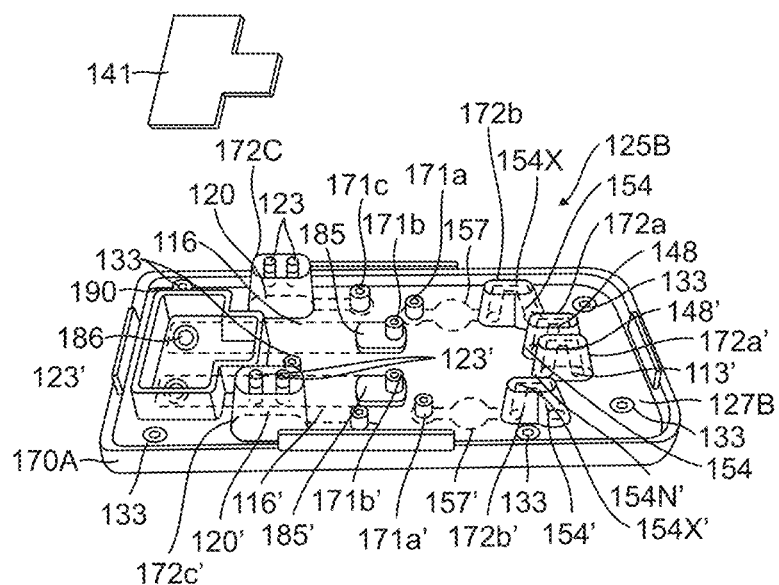
FIG. 13 is a perspective view of a bottom surface of a first housing member of the cartridge assembly of FIG. 10.

With reference to FIGS. 12 and 13, the inner surface 127A of the top member 125 has a plurality of open projections 171 and closed projections 172 providing a plurality of open fluid conduits and closed fluid conduits, respectively, with the open fluid conduits 171 passing fluid to and from the insert 180 and the closed fluid conduits 172 passing fluid along and/or through the top member 125A.

On the outer surface 126A of the top member 125A, an opening is provided for the inlet 113 that leads to the fluid conduit 148 which extends below the outer surface 126A in the closed projection 172a (FIG. 13). The fluid conduit 148 leads to the reagent chamber entry 154N formed as a shallow recessed groove along the outer surface 126A (FIG. 12). The reagent chamber 154 (containing reagent 153) is formed as a depression in projection 172b. Reagent chamber exit 154X extending under the outer surface 126A leads to the vented conduit 157. The vented conduit 157 is a shallow recessed groove extending along the outer surface 126A with the hydrophobic barrier 159 lying at the outer surface 126A. In the illustrated embodiment, the entry and the exit of the vented conduit 157 are configured below the barrier 159, and the barrier extends the entire length of the conduit 157. At the distal end of the conduit 157 is an open projection 171a which leads to the insert 180.

Figure 14A:
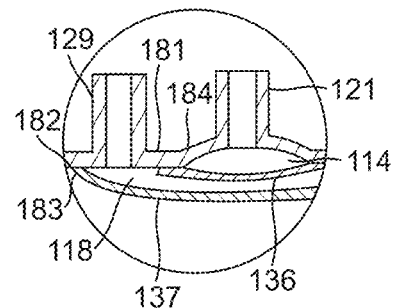
FIG. 14A is a detailed side cross-sectional view of a flexible reaction pouch and a flexible pump pouch of the insert of FIG. 14.
Figure 14:
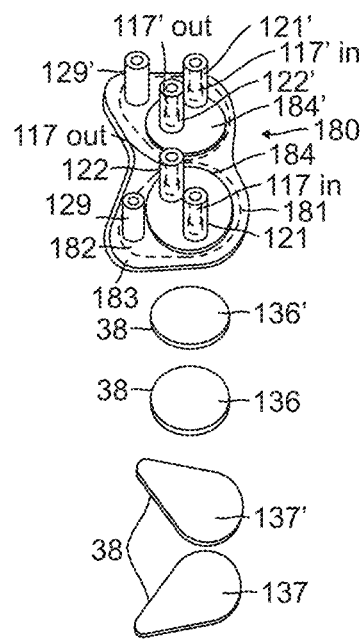
FIG. 14 is an exploded perspective view of an insert for use with the cartridge assembly of FIG. 10.

As shown in FIGS. 14 and 14A, the insert 180 has a generally rigid substrate 181 having a "butterfly" shape of two generally equal and similar halves that are mirror images of each other, with each half being for use with one of the systems T and T'. The substrate 181 can be made of any suitable material, e.g., polypropylene. The substrate 181 has a top surface 182 and a bottom surface 183, and is generally planar or flat except in two opposing interior circular regions where each region is slightly raised into a domed formation 184 and 184'. Focusing on the system T with the understanding that the following discussion also applies to the system T', the domed formation 184 of the insert 180 has two cylinders projecting from the top surface 182 to form the fluid conduits 121 and 122 for enabling fluid or the master mix to pass into and out of the flexible reaction pouch 114. In that regard, the flexible reaction pouch is formed by thin film patch 136 whose peripheral edge 138 is affixed to the bottom surface 183 under the domed formation 184 (and under the fluid conduits 121 and 122), e.g., by thermal bonding (heat sealing), ultrasonic welding and/or adhesives. The patch 136 is sized and shaped to cover and extend over at least the domed formation 184. Positioned in the fluid conduit 121 is the one-way inlet passive check valve 117IN. Positioned in the fluid conduit 122 is the one-way outlet passive check valves 117OUT.

It is understood that the substrate 181 can be flat in its entirety or raised in various geometries (e.g., rectangular channels, conical) in the two interior regions. Where raised, the bottom surface 183 to which the patches 136 and 137 are attached causes the reaction pouch 114 and the pump pouch 118 to expand toward to the bottom surface 183 which helps the pouches maintain flat contact with the heating surface 191 of the unit 165. This feature enables a sufficient fluid volume to be held in the reaction pouch 114 and the pump pouch 118 with only a slight bulging of these pouches outwardly toward the heating surface 191.

Referring back to FIGS. 12 and 13, fluid connection for flow from the vented conduit 157 down to the flexible reaction pouch 114 for amplification is made between the top member 125 and the insert 180 when the open fluid conduit 171a is inserted into the fluid conduit 121 of the insert. Fluid connection for flow from the flexible reaction pouch 114 up to the detection chamber 116 is made between the top member 125A and the insert 180 when the open fluid conduit 171b of the top member 125A is inserted into the fluid conduit 122.

The fluid conduit 171b leads to the detection chamber 116 which is formed as a shallow recessed elongated rectangular groove on the outer surface 126A of the top member 125A. The test strip 119 sits in the chamber 116. Advantageously, a proximal end of the chamber 116 where the fluid conduit 171b exits has a slightly deeper well portion 185 for collecting excess fluid to prevent flooding of the chamber 116. Moreover, at a distal end for the chamber 116, a channel 186 is provided for any additional excess or waste fluid (including air) to flow into the waste chamber 160, in which the top of the waste chamber has a vent 196 for releasing pressure to avoid any fluid leakage from over-pressurization of the cartridge. The cartridge as disclosed herein is contained such that the biological fluid samples are sealed in the cartridge to prevent amplicon contamination and contamination by biohazardous materials. As best seen in FIG. 13, the waste chamber 160 is formed in part by a panel projecting from the inner surface 127A of the top member 125A. The panel 190 forms a closed-loop configuration surrounding one or both of the channels 186 and 186'. The panel 190 is sealed by a bottom thin film sheet 141 (FIG. 13) which covers at least the closed loop configuration.

The pump pouch 118 is formed outside of the flexible pouch 114 on the insert 180. As shown in FIGS. 14 and 14A, thin film patch 137 is placed over the patch 136 and under fluid conduit 129 projecting from the top surface 182 of the substrate 181. In that regard, the patch 137 is shaped and sized so as to cover at least a portion of the patch 136 and the fluid conduit 129. Its peripheral edge 38 is affixed to the bottom surface 183 and/or the patch 136 by thermal bonding (heat sealing), ultrasonic welding, and/or adhesives.

Fluid connection between the insert 180 and the electrolytic cell 120 in the top member 125A is made when open fluid conduit 185 of the top member is inserted and received in the fluid conduit 129 of the insert. The electrolytic cell 120 is situated in an open cavity formed in closed projection 172c. Insert molded electrodes 123 extend from inside the cavity to outside the projection 172c where distal ends are exposed for connection with leads adapted to provide an electrical current to drive the electrolytic cell 120. To that end, an opening 205 (FIG. 12) is provided for the projection 172c and particularly the electrodes 123 to be accessible from outside of the housing H2.

Affixed to the outer surface 126A of the top member 125A are thin film sheets 140 which seal all of the openings on the outer surface 126 and the fluid path of the system T, including the inlet 113, the reagent chamber 154, the detection chamber 116, the electrolytic cell 120, the waste chamber 160.

As shown in FIG. 12, a spacer ring 192 may be inserted between the peripheral flanges 170A and 170B of the top and bottom members 125A and 125B. The spacer ring 192 has a predetermined thickness to increase the distance between the flanges which increases the depth of interior volume between the top and bottom members. The increase in depth varies certain parameters of the cartridge assembly 100, including the extent to which the distal ends of the electrodes 123 protrude beyond the outer surface 127B of the bottom member 125B. For example, a predetermined length of exposed electrodes is needed for making proper contact with the contact leads 152 of the unit 165 while avoiding damage to either the electrodes or the contact leads. The spacer ring 192 may be made of the same material as the top and bottom members. For alignment and interlocking engagement, recesses 193 may be provided on ring surfaces that contact the flange 170A and/or 170B which may correspondingly provide ridges 194 that are received in the recesses 193.

The insulation member 192 positioned between the top and bottom members 125A and 125B may assume a variety of shapes and sizes. The insulation member 192 may have any number of holes or recesses to accommodate the various projections extending into the interior volume between the top and bottom members. In the illustrated embodiment, the insulation member 52 sits between the insert 180 and the top member 125A, inside the spacer ring 192. The member 52 has holes 195 for the various fluid conduits of the insert 180 to pass through and connect with the open fluid projections of the top member 125A. One hole 195a is for an alignment projection 135B. The insulation member 187 serves a number of functions, including thermal insulation of the pouches 114 and 118 of the insert 180, and shock absorption for the electrodes 123 of the top member 125A when the cartridge assembly is placed in the unit 165. Any suitable insulating foam may be used, non-limiting examples of which include silicone foams (e.g., those commercially available such as from Marian, Indianapolis, Ind.).

For assembly, the cartridge assembly 100, the top member 125A and the bottom member 125B are first assembled individually before the top and bottom members are joined together, e.g., through pressure fitting (snap fitting) or a more permanent bonding method including but not limited to ultrasonic welding or gluing, in a manner that allows fluid to be passed from one member to another under the operating pressures encountered in the system without leakage.

The bottom member 126B may be assembled according to any suitable method. Focusing on the system T with the understanding that the description also applies to the system T', one method includes placing the insert 180 on the bottom member 125B and nesting it in the opening 183. The insulation member 187 is then placed on the insert 180 with its fluid conduits extending through the holes 195 of the insulation member 187. Fluid, e.g., silicone oil, may be introduced into the pump pouch 118 by injection through the fluid conduit 129. The spacer ring 192 is then positioned on the peripheral flange 170B of the bottom member 125B.

The top member 125A may be assembled according to any suitable method. Again, focusing on the system T with the understanding that the description also applies to the system T', one method includes (in any order of the following three acts) placing the reagent(s) 153 in the reagent chamber 154, placing the hydrophobic barrier 159 on the vent conduit 157, and placing the test strip 119 in the detection chamber 116. The thin film sheet 141 is placed on the panel 190 to seal the waste chamber 160. A thin film sheet 140 is placed on the outer surface 126A to seal at least the inlet 113, the reagent chamber 154, the detection chamber 116 and the electrolytic cell 120. As shown, the thin film sheet does not cover the vent conduit 157 or waste vent conduit 196.

The cartridge assembly 100 may be used in combination with a facilitator electronics unit 165, as shown in FIG. 10. For amplification, contents of reaction pouch 114 on the bottom of the cartridge assembly 100 are heated by a heat source provided in the unit 165 which has a recessed receiving portion 150 in which the card assembly 100 is placed and held by releasably locking arms 192 for thermal contact with a controlled heating surface 191 generally lining the bottom of the recessed receiving portion 150. In that regard, it is understood that an empty card assembly 100 may be placed in the unit 165 and preheated to a reaction temperature. A reaction temperature may vary depending on the selected amplification method. In some embodiments, the reaction temperature is constant, and in the range of about 37° to 70° C. In some embodiments, the reaction temperature is constant at about 63° C. In other embodiments, the reaction temperature is constant at about 55° C. The reaction temperature will vary depending on the isothermal nucleic acid amplification method used. In addition to LAMP and EXPAR, isothermal recombinase polymerase amplification (RPA) may be used having a reaction temperature of about 37° C.

In use, the cartridge assembly 100 may be placed in the unit 165 for heating. After the reaction pouch of the cartridge assembly is heated to the selected reaction temperature, a sample is injected into the inlet 113, e.g., by a syringe, through the thin film sheet 140. The sample enters the fluid conduit 148 and into reagent chamber 154 with reagent 153, e.g., a liquid or lyophilized master mix reagents. The resulting mix then passes through the vent conduit 157 where gas(es) are vented to outside the cartridge assembly 110 via the hydrophobic barrier 159 which allows gas(es) to pass while retaining fluid in the conduit 157. The vented mix then enters the reaction pouch 114 via the one-way passive inlet check valve 117IN. It is understood that the sample is introduced into the inlet 113 with sufficient pressure or injection force so as to travel into the reagent chamber 154 and through the vent conduit 157.

Contents of the reaction pouch 114 are heated by the heating surface 191 of the unit 165, thereby initiating amplification of the sample in the reaction pouch. After the contents are heated at a predetermined temperature for a predetermined duration for amplification, the unit 165 activates the electrolytic cell 120 with electrolyte 124 by energizing the electrodes 123 with an electrical current via the contact leads 152. Electrolysis in the cell 120 produces gas(es) which pass into the pump pouch 118 via the fluid conduit 129 pressurizing the pump pouch to expand and press on the patch 136 thereby compressing the flexible reaction pouch 114 against the rigid domed formation 184 of the insert 180. As a result of the compression, the contents of the reaction pouch 114 are expressed or otherwise displaced into the fluid conduit 122 via the one-way passive outlet check valve 117OUT and pass into the detection chamber 116. The outlet check valve 117OUT is actuated to allow fluid to pass into the detection chamber 116 only when pressure in the reaction pouch 114 reaches a predetermined threshold pressure. The inlet check valve 117IN prevents fluid from the reaction pouch 114 from returning to the vent conduit 157.

The pump pouch 118 may preferably contain a fluid with high thermal conduction so as to help transmit heat from the heating surface 191 to the reaction pouch 114. The fluid may also be selected to have a boiling point above the temperature used for the isothermal amplification reaction. Suitable fluids include but are not limited to water and aqueous solutions, and silicone oil.

In the detection chamber 116, the amplified fluid flows onto the test strip 119, e.g., by means of lateral flow, with any excess pooling in the well portion 185 at the proximal end of the detection chamber 116 and any further excess passing into the waste chamber 160 at the distal end of the detection chamber 116, which releases pressure through vent 196. The test strip 119 reacting to the amplified fluid provides a visual readout that is visible to the user from the detection chamber 116 through the thin film 140. In this process, fluids remain sealed within the cartridge assembly 100, eliminating amplicon carry-over contamination.

The foregoing description applies similarly to the system T' embodied in the cartridge assembly 100. As illustrated, the systems T and T' are arranged on opposite sides of the cartridge assembly 100 divided by a longitudinal axis, in mirror image of each other across the longitudinal axis. As understood by one of ordinary skill in the art, the systems may be arranged in other suitable configurations as desired or needed.

It is understood that while the above descriptions of the cartridge assemblies 10 and 100 reference direction or orientation, for example, a "top" member and a "bottom" member, the reference is merely for ease of discussion features of the invention, including movement and transport of fluid to, from and between the first and second members of the housing, and not a limitation on the system and cartridge assemblies as they may function in any direction or orientation. Moreover, while some components and structure of the systems are described as being above or below others and/or are lateral to or aligned with others, the relative positioning is also not a limitation but merely one of many possible embodiments of the system and cartridge assemblies.

It is also understood that the housings H1 and H2 need not be of a two-piece or multi-piece construction. The top and bottom members may be manufactured from a single monolithic piece, e.g. through injection molding or computerized numerical control (cnc) milling. In any case, the top and bottom members and/or the insert may be constructed from a polymer, e.g., polypropylene injection molded from USP Class VI polypropylene pellets (Pro-fax SR256M, PolyOne, Inc., Rancho Cucamonga, Calif.) using a G-100T injection molding press from Morgan Industries (Long Beach, Calif.). The preparation of the top and bottom members and/or the insert is not limited to injection molding, and can be made by any suitable technique. For example, other means for preparing may include but are not limited to cnc milling, laser cutting, or hot embossing.

Where a septum 112 is provided for an inlet 113 (FIG. 1), the septum a may be made from any suitable material that is compatible with the reaction mixture (i.e., that does not react with the reaction mixture and is not corroded by the reaction mixture) which passes through the septum. Suitable septum materials should fit securely in the inlet 113. For example, the septum may be made from silicone, or the like. To create a silicone septum, a short piece of silicone cord (e.g., from McMaster-Carr) can be inserted into the inlet 113.

The passive one-way valves 117IN and 117OUT may be any suitable passive one-way valve provided it is position in a suitable orientation that allows fluid to flow in the desired direction. In some embodiments, however, the valve is small, simple and low-cost. One exemplary valve is a one-way passive ball-and-spring valve (e.g., CCPI2510014S, the Lee Company, Westbrook, Conn.) which can be press-fit into the fluid conduits to complete the pathways to and/or from the reaction pouches and the pump pouches.

Materials suitable for construction of the patches 36, 37, 136 and 137 to form the reaction and pump pouches 114 and 118 include, e.g., a 0.005" thick flexible polypropylene film (from Qosina, Edgewood, N.Y.). Materials suitable for construction of thin film sheets 40, 140 and 141 include, e.g., polypropylene film heat-sealed onto the respective surface. The polypropylene film may be constructed using a custom-built heat press, with aluminum dies, custom cut to produce desired shapes and sizes, attached to a temperature-controlled aluminum block mounted to an arbor press for safety and leverage. For example, for each reaction pouch 14 and 114 depicted in the Figures, the aluminum die used to adhere the peripheral edge 38 of the patches 36 and 136 to the bottom surface 183 of the insert substrate 181 has a generally circular, ring-like shape that when heated and pressed against the film and the substrate heat-seals the portion of the film contacting the ring-like shape of the die to the substrate. Similarly, for each pump pouch 18 and 118 depicted herein, the aluminum die used to adhere the peripheral edge 38 of the patches 37 and 137 to the bottom surface 183 of the insert substrate 181 has the general triangular shape (and larger than the ring-like shaped die used to create the reaction pouches) such that when heated and pressed against the film and the substrate heat-seals the portion of the film contacting the outline of the die to the substrate. While certain shapes and sizes of the pouches and the dies are described and illustrated here, it is understood that the pouches and dies can take any suitable shape and size.

Fluidic Control

As disclosed herein, the cartridge assemblies according to embodiments of the present invention use two-layer pouches in conjunction with electrolytic pumping. As opposed to other conventional clinical diagnostic systems that rely on flexible pouches, embodiments of the present invention do not require external pistons or actuators. The electrolytic cell is part of the cartridge assemblies according to embodiments of the present invention, which enables compact and inexpensive instrument design, since the instrument only requires electrode connectors and a current source to control pumping.

As an example, with reference to FIG. 4, two small septum chambers 20, 20' (Qosina) were press fit into the openings of cards 25A and 25B of the cartridge (10). Standard 18.5 gauge stainless steel syringe needle tips were used to fill the chambers and pump pouches with a 1M aqueous $Na_2SO_4$ electrolytic solution through the septum on top of the electrolyte chamber. The two needles were then capped closed, but were left in the septum chamber to be used as electrodes for electrolytic pumping.

The flow rate during electrolytic pumping can be adjusted based on the applied current. For example, it was determined that an amplified reaction mix should be pumped from the reaction chamber into the lateral flow strip chamber at a flow rate of approximately 100 µL/min to ensure that the lateral flow strip runs properly. For example, applied current has an approximately linear relationship with (i.e., it is proportional to) the flow rate during electrolytic pumping in the cartridge systems made according to embodiments of the present invention. An applied current of 50 mA provides a suitable flow rate in the cartridge, however, the present invention is not limited to that flow rate. The effective flow rate will vary depending on the size and materials selected for the cartridge. Accordingly, a person having ordinary skill in the art can easily determine the effective flow rate for a cartridge system made according to various embodiments of the present invention.

In some embodiments, a cartridge (100) includes an integrated electrolytic pump. Use of an electrolytic pump is well known and is described in Bohm et al., 1999, *Biomedical Devices*, 1:121-130, the entire contents of which are herein incorporated by reference.

Fluid handling in the cartridges according to embodiments of the present invention relies on one-way valves to prevent the fluid within the reaction chambers (pouches) from leaking prematurely into the lateral flow detection chambers (pouches). For example, injecting 75-100 µL liquid into the reaction chamber (pouch) of cartridge (10) as shown in FIG. 4 resulted in <2 psi fluid pressure, which is less than the cracking pressure of the valves used in the cartridge. Therefore, fluid is retained in the reaction pouch until electrolytic pumping forces the fluid through the passive valve and onto the lateral flow strip. For example, valves inserted into a cartridge (10) as shown in FIG. 4, crack at 2 psi. A volume of 15-25 µL was unrecoverable when pumped through the valve configuration in the detection fluid conduit of the reaction pouch. However, the dead volume on the cartridge inlet port containing a septum is negligible.

Any suitable check valve may be used in the cartridge systems disclosed herein. In some embodiments, to implement fluid control in a cartridge as disclosed herein includes a check valve as described in U.S. application Ser. No. 13/859,680 filed on Apr. 9, 2013 and titled CHECK VALVE, the entire contents of which are herein enclosed by reference. A one-way passive check valve as disclosed in U.S. application Ser. No. 13/859,680 includes of a short piece of rigid core tubing with one closed end, and a side port cut into the core to provide an alternate outlet. An elastomeric silicone tubing sleeve is placed over the rigid core, covering the side port. The sleeve inner diameter is slightly smaller than the core outer diameter, which results in a small but controllable radial pressure exerted by the sleeve onto the core. As fluid is injected through the open end of the core tubing, it has to expand the sleeve before it can flow out of the side port, resulting in a non-zero but controllable outlet pressure. In the cartridge shown in FIG. 12, the inlet valve and outlet valve were fabricated from rigid PEEK™ (Zeus, Inc.) plastic tubing with nominal outer diameter of 1.59 mm, melted closed at one end, and containing a side port opening. Elastomeric cast molded silicone tubing sleeves were placed over the core, covering the side port. Silicone tubing sleeves with 1.4 mm inner diameter and 430 µm wall thickness produced an opening pressure in the range of 3-4 PSI for the inlet valves. Sleeves with 1.2 mm inner diameter and 430 µm wall thickness produced higher opening pressure in the range of 6-8 PSI for the outlet valves. For these valves, the initial cracking pressure is ~0.5-3 PSI larger than the steady state opening pressure. The assembled valves were incorporated into the reaction insert by press fitting.

Heat Control of the Cartridge System

Accurate thermal control of the reaction fluid is required for appropriate device performance. This includes maintaining an appropriate and uniform temperature throughout the reaction pouch and during the entire amplification period. If the temperature is too low, isothermal amplification slows down or does not occur. For example, when using LAMP as an isothermal amplification method, if the temperature goes above about 70° C., the Bst polymerase may denature. Further, temperature variability within the reaction pouch leads to non-uniform amplification kinetics.

For thermal control of a cartridge 10, 100 any suitable heater may be used. For example, an inexpensive heater may be assembled using a custom printed circuit board (PCB) and readily available electronic components. This approach is cost effective and scalable, and the electronics may be easily miniaturized. The thin-film heater used requires approximately 0.7 Watts to maintain a steady state temperature of 63° C. on the heater surface. Cartridge systems according to embodiments of the present invention may run off line power, or due to its low power consumption, may be easily adapted for battery operation.

With a cartridge 10 on a heating surface, air that may become trapped between the cartridge and the heater, for example if the cartridge does not sit completely flat on the heater, significantly lowers the thermal conductivity, which may contribute to non-uniform fluid heating within the reaction pouch. If the pump pouch is not filled with liquid, then additional air is trapped in the pump pouch underneath the reaction pouch. The temperature of the liquid in the reaction pouch was measured using a thermocouple inserted through the septum inlet. If the pump pouch is empty, then the fluid temperature in the reaction pouch deviates significantly from the temperature measured directly on the heater surface underneath the cartridge, as indicated in the graph of FIG. 15. Filling the pump pouch with a medium of higher thermal conductivity than air, such as electrolyte solution, improves the thermal transfer efficiency between the heater and the cartridge, resulting in faster heating and a final temperature closer to the desired set point. The reaction pouch reaches a stable temperature of 62±0.1° C. within approximately ten minutes.

According to results obtained from modeling the thermal behavior of the cartridge in three dimensions using COMSOL Multiphysics, the temperature within the reaction pouches deviated from a temperature of 63° C. by less than 0.5° C. throughout the reaction chamber (pouch) when the cartridge made ideal contact with the heater surface with no air gap in the system (FIG. 16A). The plastic structures above the reaction pouches and a small air pocket intentionally introduced at the outlet port within the reaction pouch did not produce significant temperature deviations. To understand the effects of non-ideal thermal contact, the system was modeled with a 150 µm thick thermally resistive air layer between the pumping pouches and the heater surface (FIG. 16B). This resistive layer significantly reduces the heat transfer between the heater and the cartridge, decreasing the maximum temperature in the reaction pouches by 1° C., and leading to more significant temperature variations throughout the reaction pouch.

In some embodiments, a cartridge 10 is placed in a reusable heater that is fabricated to precisely control the temperature on the bottom side of the cartridge where the reaction pouches are exposed. A heater as shown in FIG. 9 was fabricated for the cartridge 10, inset in the heater. The chassis of the heater 65 in FIG. 9 was printed using a fused deposition modeling machine. Thin-film polyimide heaters were attached to the underside of an aluminum plate to provide as the heater surface within the device, to provide evenly-distributed heating. Polyurethane foam sealant inside the heater minimizes the power required to reach and maintain the reaction temperature. The temperature was controlled with a custom electronic circuit on a printed circuit board (PCB) using feedback from a thermistor embedded in the aluminum plate. The instrument used approximately 8 watts (W) during the initial approximately 3 minutes of heating ramp, and approximately 0.5 W to maintain the temperature.

Figure 17:
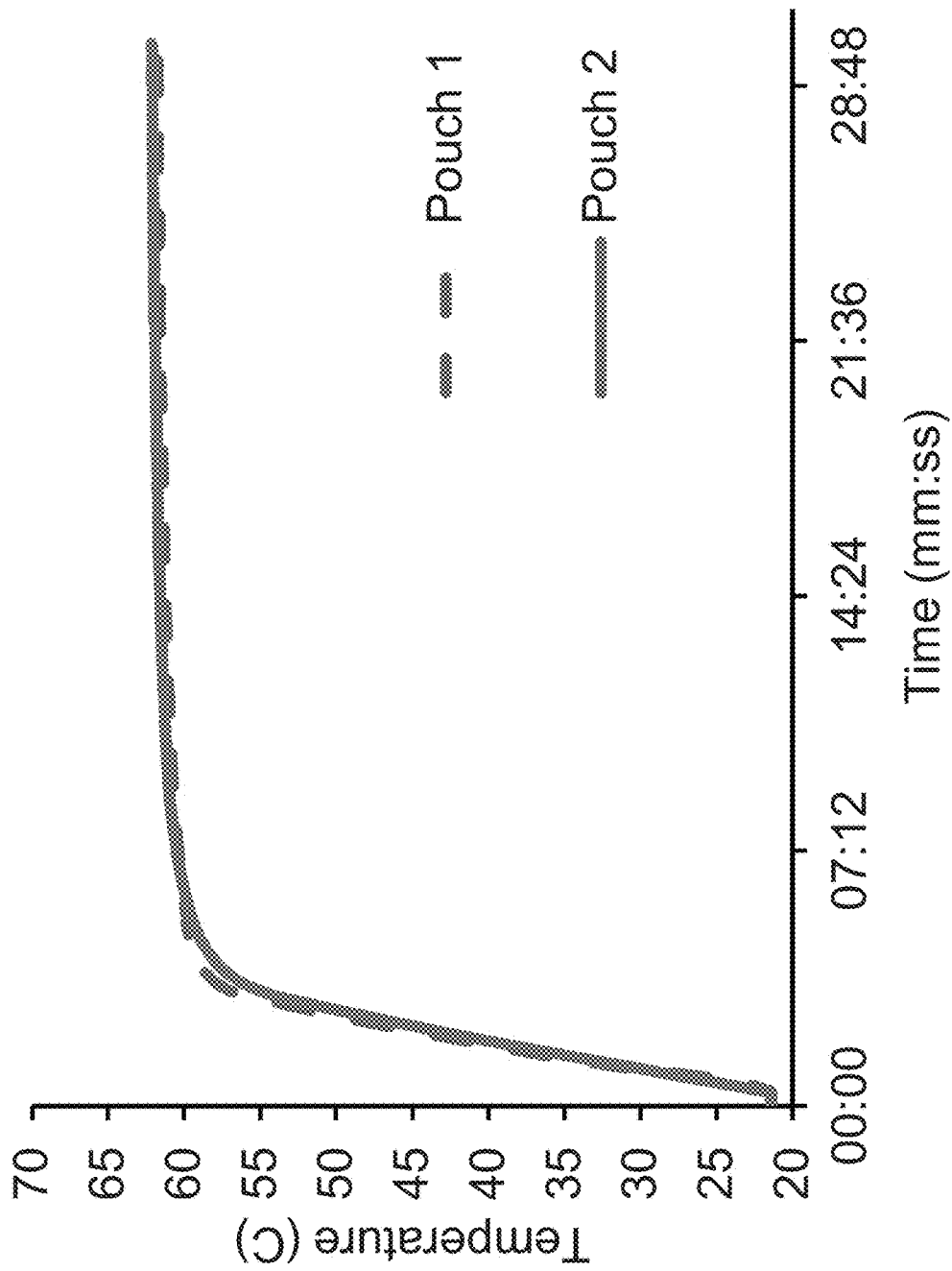
FIG. 17 is a graph of temperature as function of time showing the heating efficiency of the reaction buffer within both reaction pouches 114 of a cartridge 100, according to embodiments of the present invention.

In some embodiments, a cartridge 100, contains thermal insulation above the insert 180 to facilitate appropriate thermal control and the bottom of the insert is designed to protrude below the cartridge by about 400 µm, to facilitate appropriate thermal contact with a heater surface located underneath the insert. The pump pouches are completely filled with silicon oil and slightly inflated. Therefore, the liquid filled pump pouches (enclosing the reaction pouches) are pushed against the heater surface, which ensures good thermal contact between the heater and the pump and reaction pouches. Efficient heating of the reaction buffer within both reaction pouches of a cartridge 100 was measured to reach the targeted temperature within approximately 10 minutes as shown in the graph in FIG. 17. The temperature is maintained at steady state over the duration of the isothermal amplification.

Amplification and Detection in the Cartridge

Figure 18C:
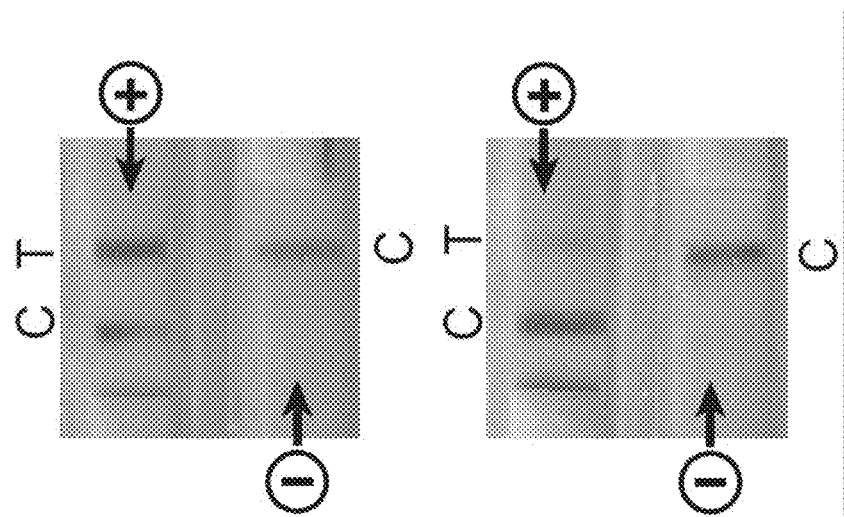
FIG. 18C is a photograph of a NALF test strip of EXPAR amplicons of human genomic DNA as the control indicated by the minus sign and M.tb genomic DNA indicated by the plus sign amplified by EXPAR, according to embodiments of the present invention.
Figure 18B:
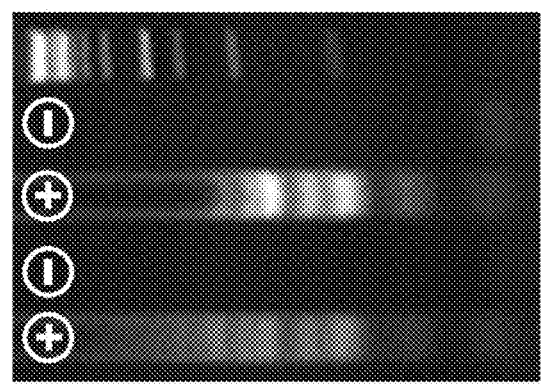
FIG. 18B is a photograph of a gel electrophoresis of the samples detected in FIGS. 18A and 18B.
Figure 18A:
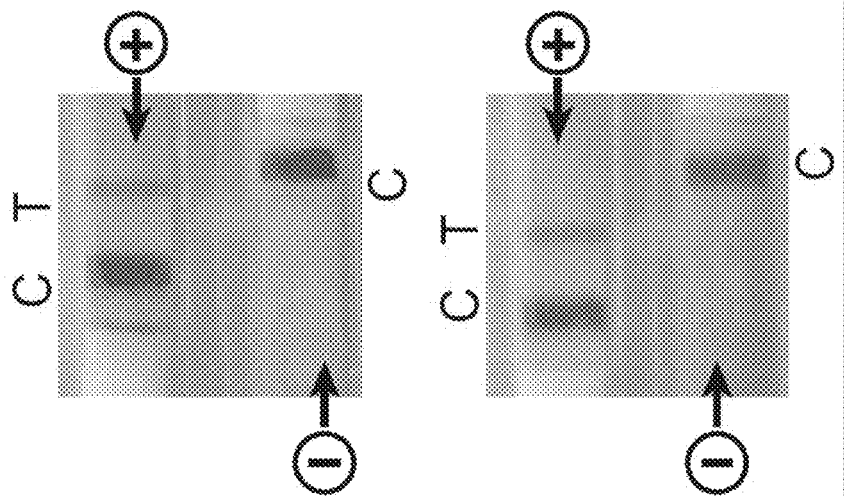
FIG. 18A is a photograph of a NALF test strip of LAMP amplicons of human genomic DNA as the control indicated by the minus sign and M.tb genomic DNA indicated by the plus sign amplified by LAMP, according to embodiments of the present invention.

LAMP and EXPAR coupled to NALF detection was performed using a cartridge 10 and a heater 65. For these experiments, the heater setpoint was adjusted for the desired reaction temperature (63° C. for LAMP and 55° C. for EXPAR), and a cartridge with empty reaction chambers was allowed to pre-heat on the heater for ten minutes. Mastermix was then injected through the inlet ports into the reaction chambers, with one positive and one negative reaction per cartridge. For LAMP, positive reactions contained 3000 copies of *Mycobacterium tuberculosis* (M.tb) genomic DNA, while for EXPAR, positive reactions contained $6 \times 10^5$ copies of M.tb genomic DNA. In both cases, negative reactions contained no M.tb genomic DNA, but all reactions included 10 ng human genomic DNA, which is present as background in clinical samples. The assays are not cross-reactive with human genomic DNA. The master-mix solutions in the reaction chambers were allowed to incubate on the heater for 10 minutes (LAMP) or 60 minutes (EXPAR), then current was applied to the electrolytic pumps, to push the amplified reaction mastermix through the outlet fluid conduit and into the chamber containing the lateral flow strips for detection. The final readouts for LAMP-NALF (FIG. 18A) and EXPAR-NALF (FIG. 18C) consisted of the expected two lines for the positive and a single control line for the negative reactions. For LAMP, analysis of master-mix amplified in the cartridge via gel electrophoresis revealed that master-mix amplified in the cartridge produces the same characteristic pattern of high molecular weight amplicons as control reactions performed under standard conditions (FIG. 18B).

The following Examples are presented for illustrative purposes only, and do not limit the scope or content of the present application.

EXAMPLES

Example 1. Fluidic Control of Reaction Pouch Filling

Figure 19:
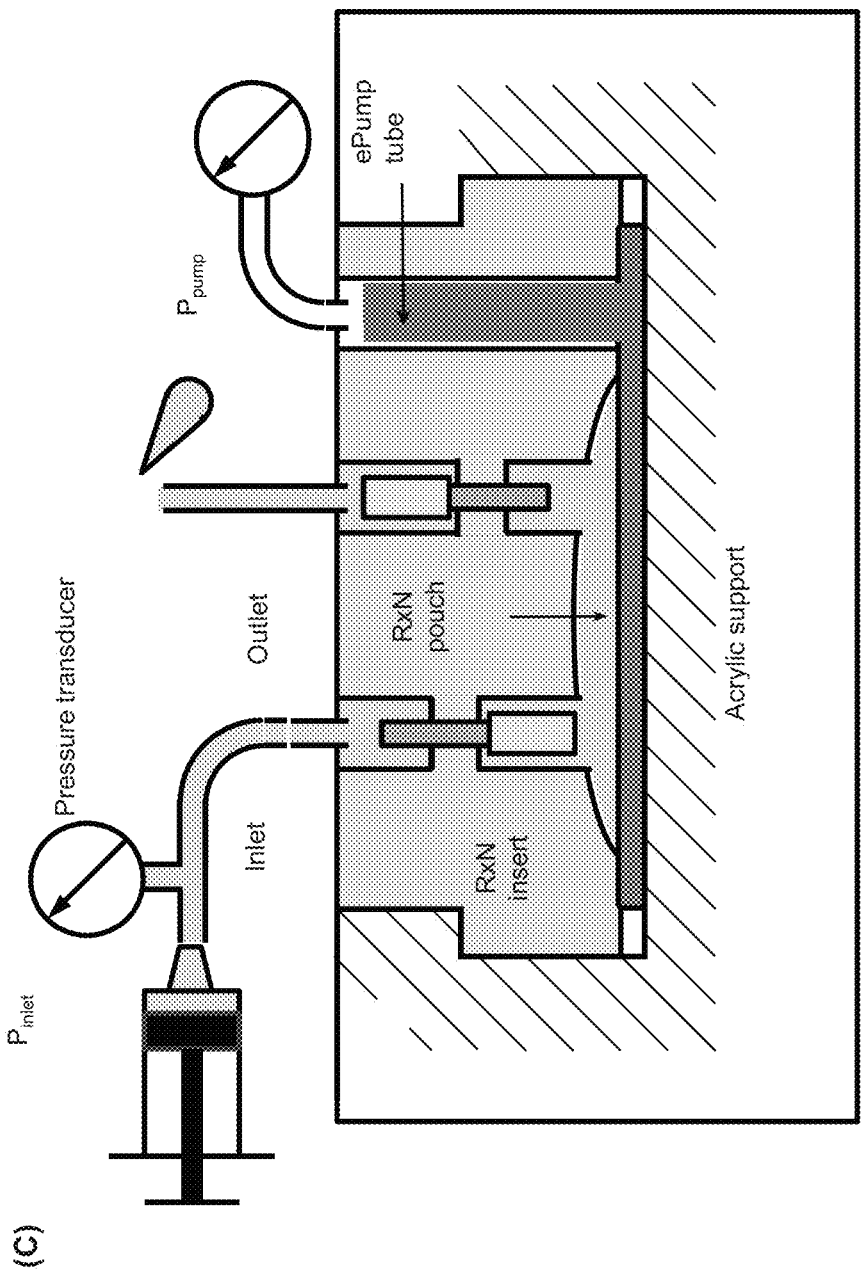
FIG. 19 is a schematic showing how the fluidic control and pressure of a cartridge 100 was monitored.
Figure 20:
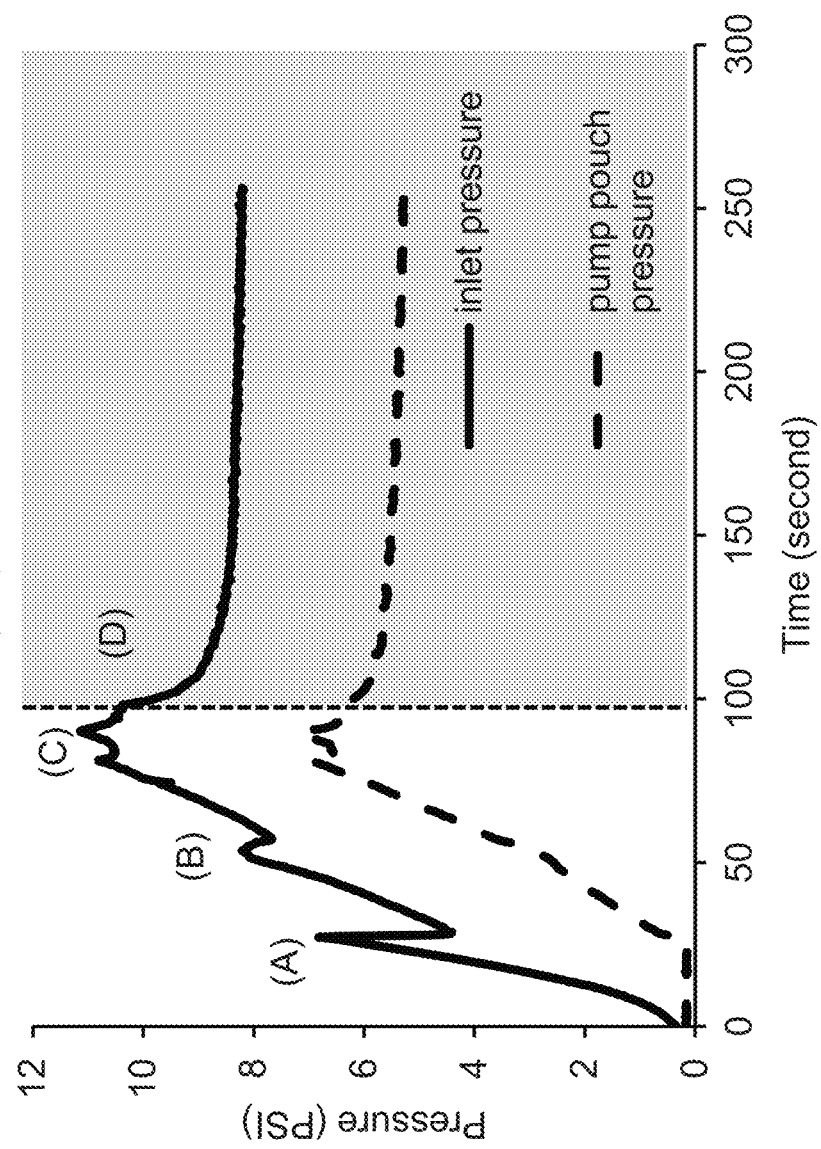
FIG. 20 is a graph of pressure versus time throughout an assembled cartridge system 100, according to embodiments of the present invention.

To characterize the fluidic control of master-mix entering and exiting the reaction pouch through the valves 117IN and 117OUT in assembled inserts 180, fluid was injected into the fluid conduit 121 with an assembled reaction insert 180 using a syringe pump, at 3 µL/sec for 91 sec, and the pressure upstream of the inlet port to the reaction pouch was monitored, as shown in FIG. 19. In addition, the pressure was monitored at the fluid conduit 129 connected to the filled pump pouch 118 as surrogate to the pressure in the reaction pouch 114. As the buffer fills the reaction pouch, no further stretching of the polypropylene films covering the reaction or pump pouches is required. However, at the beginning of the experiment, the reaction pouch is empty with the reaction pouch film pressed up against the dome of the reaction chamber, and the pump pouch is fully filled. As the reaction pouch is filled, a similar volume of pump pouch fluid is forced out of the pump pouch outlet and pressurizes the enclosed electrolytic pump chamber. Therefore, it is assumed that the pressure measured at the closed pump pouch outlet approximately reflects the pressure in the reaction pouch. For this experiment, four replicates all showed similar behavior, an example of which is shown in FIG. 20. Approximately 30 µL of compressible air ahead of the liquid causes slow pressurization at the inlet at the start of the pumping. The inlet pressure then built up while the pump pouch pressure remained at zero, until the opening pressure of the inlet valve was reached (peak (A) of FIG. 20), followed by a pressure drop as the fluid rushed into the reaction pouches. As the reaction pouch filled with liquid, the inlet pressure and pump pouch pressure both increased (peak (B) of FIG. 20), but the difference between the two pressure measurements remained constant at around 4 PSI, which is the required opening pressure of the inlet valve. Eventually, the cracking pressure of the outlet valve was reached (peak (C) of FIG. 20), and the fluid began to exit through the fluid conduits, serving as outlet for fluid exiting the reaction pouch 114. The outlet valves opened at around 6 PSI pressure difference between the pump pouch 118/reaction pouch 114, and open atmosphere. After fluid exited the fluid conduit, the pump was turned off, as indicated by the grey area (peak (D) of FIG. 20). In these four replicates, 250±60 μL of reaction buffer could be pumped into the reaction pouch between the opening events at the inlets and outlet valves, more than adequate to accommodate the desired assay volume of 100 μL per reaction.

Example 2. Electrolytic Pumping

As described in Bohm et al., 1999, the pumping rate of an electrolytic pump is approximately proportional to the applied current. The handheld electrode device as disclosed herein includes controllable current sources to power an electrolytic pump, and is capable of generating a constant current with a resolution of 2.7 mA up to 700 mA. The lower end of this current range will be used to power the ePumps in the amplification and detection unit. Relevant to the amplification and detection unit, it was determined that by applying 8.2 mA or 13.7 mA of current to the ePumps, the outlet valve opened within 98 or 57 seconds, respectively from the start of electrolysis. In both cases, the fluid exited the reaction pouch at a flow rate of approximately 2-4 uL/s, which is approximately in the required range to enable suitable lateral flow performance.

Example 3. Venting of Dead Air in Cartridge 100

Figure 21:
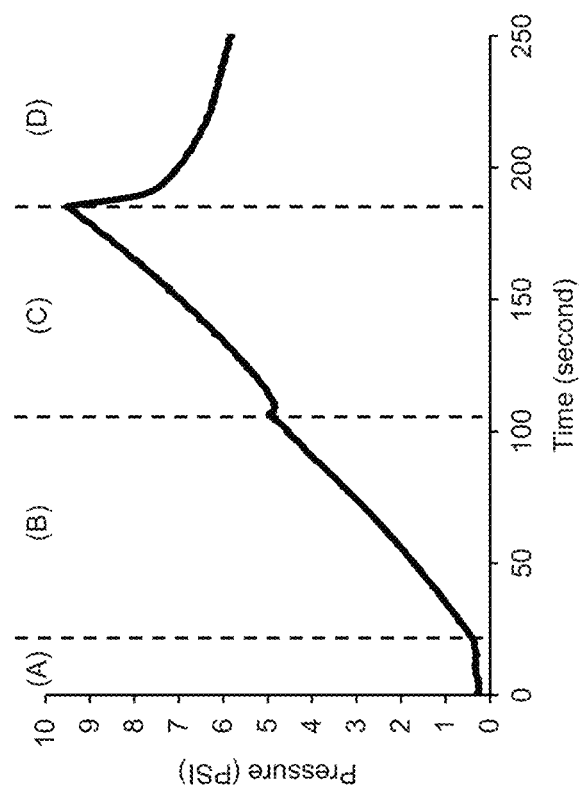
FIG. 21 is a graph of pressure versus time upstream of the venting barrier 159 to measure the amount of dead air in the cartridge, according to embodiments of the present invention.

Proper venting of the dead air upstream of the reaction pouch affects the reproducibility of the amplification reaction, as large gas bubbles introduced into the reaction pouch may interfere with heat transfer and temperature equilibration throughout the master-mix volume in the reaction pouch. For venting the air upstream of the insert 180 in the cartridge 100, a PTFE (polytetrafluoroethylene) porous membrane with 0.2 μm pores, on polypropylene mesh backing was used as the venting material for the venting region. This membrane was heat sealed on top of the polycarbonate channels immediately upstream of the connection to the reaction fluid conduits of the insert 180. To test proper performance of this venting approach, 150 μL of reaction buffer fluid was injected into the sample input port 113 of the cartridge 100 using a syringe pump, with air in the fluid channel upstream and downstream of this liquid bolus. In this experiment, the reaction pouch outlet 122X and pump pouch fluid conduit 129 was closed, thus liquid could enter into the reaction pouch 114 through the reaction inlet 121N containing a check valve 117N, but could not exit from the reaction pouch 114. During this experiment, the pressure in the fluid channel 148, 154 upstream of the vent conduit 157 was measured (FIG. 21). The barrier 159 vents the dead air ahead of the fluid injected into the cartridge. At this time, represented by peak (A) in FIG. 21, no pressure builds up in the fluid channel, and no air is injected through the inlet port 121N into the reaction pouch 114. The venting barrier 159 closes as liquid fills the area underneath the venting barrier. At this time, represented by peak (B) in FIG. 21, pressure builds up in the fluid channel 154X until the inlet valve 117IN opens. At this time, represented by peak (C) in FIG. 21, the fluid is pumped into the reaction pouch 114 through the inlet port 121N containing the valve 117IN. The channel 121 continues to pressurize due to the pressure exerted by the filled and closed pump pouch 118. At this time, represented by peak (D) in FIG. 21, after ~100 μL liquid is injected into the reaction pouch, the gas plug behind the injected volume is vented through the venting barrier 159 and the remainder of the volume is trapped in the vented portion. No air is injected into the reaction pouch.

Example 4. Process and Assay Execution in Cartridge 100

The entire process consists of the following steps. An empty cartridge is attached to the instrument, which is then powered up. At that point, the heater LED blinks to indicate system initialization, and the system performs an electrolytic pump check: if proper connections between the instrument and the electrolytic pump are established, then the two pump LEDs blink three times. The heater LED then turns solid red while the heater warms up to the programmed temperature. The heater LED turns green once the final heater temperature has been reached. At that point, in initial experiments performed in the current cartridge configuration, the sample including mastermix reagents is manually injected into the cartridge inlet port 113, and pushed into the reaction pouch 114, with venting of dead air as previously described. The master mixture 115 remains in the reaction pouch chambers to incubate at the set temperature for the desired reaction time, at which point the reaction electrolytic pumps are turned on. Once suitable pressure is built up within the pump pouches, the fluid in the reaction pouches will be forced through the outlet valves and into the lateral flow strip pouches. As discussed herein, in order to ensure that the lateral flow strip performance is not compromised by a rapid outflow of fluid from the reaction pouch, each lateral flow chamber features a recessed region to pool the incoming buffer. The sample pad extends into this pool, which enables controlled absorption of the amplified buffer into the lateral flow strip to allow proper reconstitution of the dried reagents for detection.

Figure 22:
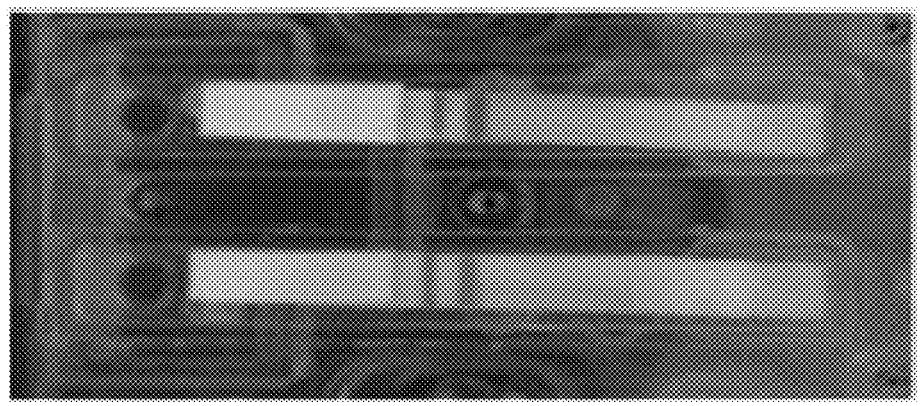
FIG. 22 is a photograph of two lateral flow test strips showing detection of a synthetic amplification product in order to demonstrate appropriate fluidic handling in the cartridge, according to embodiments of the present invention.
Figure 23:
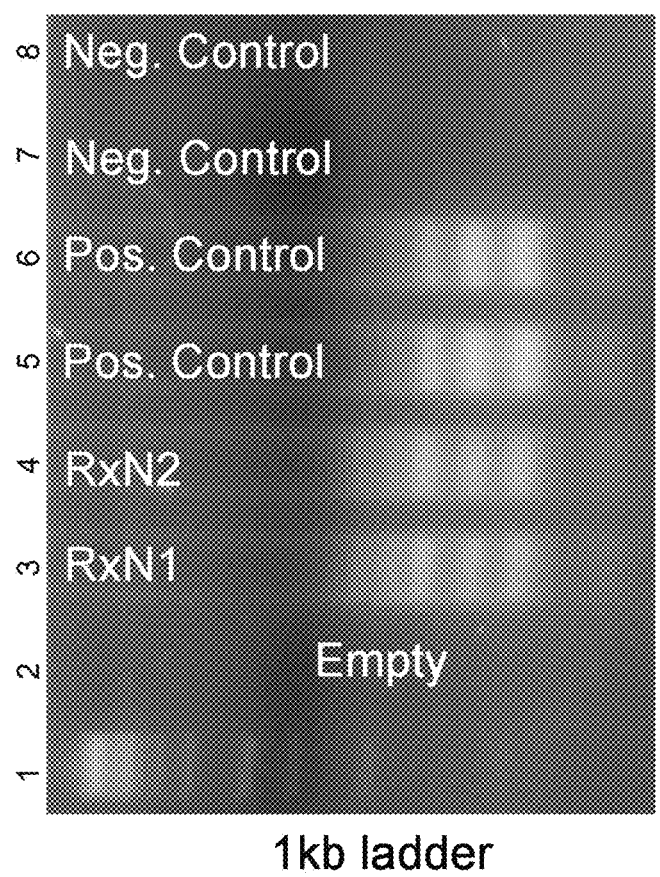
FIG. 23 is a photograph of an electrophoresis gel showing the presence of and banding characteristics of the reaction samples, positive controls and negative controls, as described herein.

To demonstrate appropriate fluidic handling in the cartridge, a mock experiment was performed, using reaction buffer spiked with a synthetic amplification product that can be detected on the lateral flow strip. The process execution, including heating, timing, and pumping, was automated by the base instrument containing a microcontroller. A suitable visual readout was obtained, as shown in FIG. 22. Furthermore, an initial proof of principle experiment was conducted to demonstrate that a LAMP reaction can be executed successfully in the cartridge 100. To verify proper amplicon formation, this first experiment utilized gel electrophoresis rather than lateral flow based detection. As described above, an empty cartridge in connection with a facilitator electronics unit was turned on for at least 10 minutes for the heater and cartridge to reach reaction temperature. LAMP mastermix with 3000 copies of *Mycobacterium tuberculosis* genomic DNA was injected into the sample input port 113 of cartridge 100, and pushed into the reaction pouch 114. The reaction was then incubated on the base instrument for about 1 hour. After incubation, amplified master-mix was withdrawn from the cartridge and analyzed via gel electrophoresis, the results of which are shown in FIG. 23. Both reaction pouches generated the expected ladder of high molecular weight concatenated amplicons expected for LAMP, with banding patterns similar to control reactions that were performed in standard reaction tubes.

As shown, for example, in FIGS. 9, 10, 11, and 12, and discussed throughout, an efficient device and method is provided for amplification and detection of nucleic acids in a fully enclosed cartridge on a portable, low-power heater. Many isothermal nucleic acid amplification reactions may be coupled to a mean of detection, and the cartridge systems according to embodiments of the present invention can be easily adjusted to accommodate different isothermal amplification methods that target different pathogens.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A biological diagnostic cartridge system, comprising:
a cartridge comprising:
    an inlet;
    a flexible reaction pouch downstream of the inlet, the flexible reaction pouch for housing a reaction liquid sample, the flexible reaction pouch having a first side and a second side, the first side directly contacting a rigid substrate;
    a flexible pump pouch for housing a thermally conductive liquid and compressing the flexible reaction pouch, the flexible pump pouch directly contacting and covering all of the second side of the flexible reaction pouch; and
a heating element in direct contact with the flexible pump pouch, the flexible pump pouch positioned between the heating element and the second side of the flexible reaction pouch.

2. The cartridge system of claim 1, wherein the cartridge further comprises:
    a detection chamber downstream of the flexible reaction pouch;
    a first fluid path from the inlet to the flexible reaction pouch; and
    a second fluid path from the flexible reaction pouch to the detection chamber.

3. The cartridge system of claim 2, wherein each of the first and second fluid paths is one-directional.

4. The cartridge system of claim 2, wherein the cartridge further comprises a first flow strip positioned in the detection chamber.

5. The cartridge system of claim 4, wherein the cartridge further comprises a second inlet, a second flexible reaction pouch downstream of the second inlet, a second flexible pump pouch adapted to compress the second flexible reaction pouch, a second detection chamber downstream of the second flexible reaction pouch.

6. The cartridge system of claim 5, wherein the cartridge further comprises a second flow strip arranged antiparallel or parallel to a first flow strip.

7. The cartridge system of claim 1, wherein the cartridge further comprises an outlet, the outlet comprising an outlet one-way passive check valve having a cracking pressure, wherein when the flexible reaction pouch houses the reaction liquid, the flexible reaction pouch has a fluid pressure, and wherein the cracking pressure of the outlet one-way passive check valve is greater than the fluid pressure of the flexible reaction pouch.

8. The cartridge system of claim 7, wherein the cracking pressure of the outlet one-way passive check valve is from about 2 to about 8 psi.

9. The cartridge system of claim 7, wherein the inlet comprises an inlet one-way passive check valve having a cracking pressure lower than the cracking pressure of the outlet one-way passive check valve.

10. The cartridge system of claim 7, wherein the cartridge further comprises a detection chamber, wherein the outlet one-way passive check valve is downstream of the reaction pouch and upstream of the detection chamber.

11. The cartridge system of claim 1, further comprising a housing; and
a pump adapted to inflate the flexible pump pouch, wherein the housing comprises a port for receiving the pump.

12. The cartridge system of claim 11, wherein the pump comprises an electrolytic pump adapted to generate gas.

13. The cartridge system of claim 1, wherein the cartridge further comprises a vent downstream of the inlet and upstream of the flexible reaction pouch.

14. The cartridge system of claim 13, wherein the vent comprises a hydrophobic barrier.

15. A portable biological diagnostic system, comprising:
a cartridge, comprising:
    an inlet adapted to receive a sample;
    a flexible reaction pouch downstream of the inlet for housing a reaction liquid, the flexible reaction pouch having a first side and a second side, the first side directly contacting a rigid substrate;
    a flexible pump pouch for housing a thermally conductive liquid and compressing the flexible reaction pouch, the flexible pump pouch directly contacting and covering all of the second side of the flexible reaction pouch; and
    a detection chamber downstream of the flexible reaction pouch;
a pump to inflate the flexible pump pouch;
a heating element in direct contact with the flexible pump pouch, the flexible pump pouch positioned between the heating element and the second side of the flexible reaction pouch; and
a power source to drive the pump.

16. The system of claim 15, wherein the pump comprises an electrolytic pump.

17. The system of claim 15, further comprising a controller configured to control activation of the heating element and the power source.

* * * * *